United States Patent
Shi et al.

(10) Patent No.: US 7,435,542 B2
(45) Date of Patent: Oct. 14, 2008

(54) EXHAUSTIVE SELECTION OF RNA APTAMERS AGAINST COMPLEX TARGETS

(75) Inventors: Hua Shi, Ithaca, NY (US); John T. Lis, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 390 days.

(21) Appl. No.: 10/602,837

(22) Filed: Jun. 24, 2003

(65) Prior Publication Data
US 2004/0053310 A1 Mar. 18, 2004

Related U.S. Application Data

(60) Provisional application No. 60/391,255, filed on Jun. 24, 2002.

(51) Int. Cl.
C12Q 1/68 (2006.01)
C12P 19/34 (2006.01)

(52) U.S. Cl. .......................................... 435/6; 435/91.2

(58) Field of Classification Search ....................... None
See application file for complete search history.

(56) References Cited

U.S. PATENT DOCUMENTS

| | | | |
|---|---|---|---|
| 4,971,902 A | 11/1990 | Nepom | |
| 5,270,163 A | 12/1993 | Gold et al. | |
| 5,473,060 A | 12/1995 | Gryaznov et al. | |
| 5,571,903 A | 11/1996 | Gryaznov | |
| 5,582,981 A | 12/1996 | Toole et al. | |
| 5,593,835 A | 1/1997 | Rando et al. | |
| 5,594,121 A | 1/1997 | Froehler et al. | |
| 5,614,503 A | 3/1997 | Chaudhary et al. | |
| 5,631,146 A | 5/1997 | Szostak et al. | |
| 5,639,595 A | 6/1997 | Mirabelli et al. | |
| 5,643,890 A | 7/1997 | Iversen et al. | |
| 5,645,985 A | 7/1997 | Froehler et al. | |
| 5,656,739 A | 8/1997 | Cubicciotti | |
| 5,658,738 A | 8/1997 | Nadeau et al. | |
| 5,681,702 A | 10/1997 | Collins et al. | |
| 5,683,987 A | 11/1997 | Smith | |
| 5,688,670 A | 11/1997 | Szostak et al. | |
| 5,712,127 A | 1/1998 | Malek et al. | |
| 5,756,291 A | 5/1998 | Griffin et al. | |
| 5,792,613 A | 8/1998 | Schmidt et al. | |
| 5,840,867 A | 11/1998 | Toole et al. | |
| 5,861,501 A | 1/1999 | Benseler et al. | |
| 6,010,884 A | 1/2000 | Griffiths | |
| 6,344,321 B1 * | 2/2002 | Rabin et al. ..................... | 435/6 |
| 6,544,741 B1 * | 4/2003 | Mugasimangalam ........... | 435/6 |

FOREIGN PATENT DOCUMENTS

| | | |
|---|---|---|
| EP | 0 710 668 A2 | 5/1996 |
| EP | 0 775 745 A2 | 5/1997 |
| EP | 0 784 984 A2 | 7/1997 |
| WO | WO 94/06811 | 3/1994 |
| WO | WO 95/11910 | 5/1995 |
| WO | WO 96/40159 | 12/1996 |
| WO | WO 97/20031 | 6/1997 |

OTHER PUBLICATIONS

Murate et al., "Up-Regulation of Acid Sphingomyelinase During Retinoic Acid-Induced Myeloid Differentiation of NB4, a Human Acute Promyelocytic Leukemia Cell Line," *Journal of Biological Chemistry* 277(12):9936-9943 (2002).
Ellington, A.D., "RNA Selection. Aptamers Achieve the Desired Recognition," *Curr. Biol.* 4(5):427-429 (1994).
Yamamoto et al., "In vitro Selection of RNA Aptamers That Can Bind Specifically to Tat Protein of HIV-1," *Nucleic Acids Symp. Ser.* 34:145-146 (1995).
Tian et al., "Dissecting Protein:Protein Interactions Between Transcription Factors With an RNA Aptamer," *RNA* 1(3):317-326 (1995).
Burgstaller et al., "Structural Probing and Damage Selection of Citrulline- and Arginine-specific RNA Aptamers Identify Base Proteins for Binding," *Nucleic Acids Res.* 23(23):4769-4776 (1995).
Symensma et al., "RNA Aptamers Selected to Bind Human Immunodeficiency Virus Type 1 Rev in vitro are Rev Responsive in vivo," *J. Virol.* 70(1):179-187 (1996).
Conrad et al., "In vitro Selection of Nucleic Acid Aptamers That Bind Proteins," *Methods Enzymol.* 267:336-337 (1996).
Hale et al., "Protein Synthesis Editing by a DNA Aptamer," *Proc. Natl. Acad. Sci. USA* 93(7):2755-2758 (1996).
Ye et al., "Deep Penetration of an Alpha-helix into a Widened RNA Major Groove in the HIV-1 Rev Peptide-RNA Aptamer Complex," *Nat. Struct. Biol.* 3(12):1026-1033 (1996).
Li et al., "RNA Aptamers for Yeast Ribosomal Protein L32 Have a Conserved Purine-rich Internal Loop," *RNA* 3(3):245-254 (1997).
Moine et al., "The RNA Binding Site of S8 Ribosomal Protein of *Escherichia coli*:Selex and Hydroxyl Radical Probing Studies," *RNA* 3(3):255-268 (1997).
Eaton et al., "Post-SELEX Combinatorial Optimization of Aptamers," *Bioorg. Med. Chem,* 5(6):1087-1096 (1997).
Gilbert et al., "RNA Aptamers That Specifically Bind to a K Ras-derived Farnesylated Peptide," *Bioorg. Med. Chem.* 5(6):1115-1122 (1997).

(Continued)

*Primary Examiner*—Kenneth R. Horlick
*Assistant Examiner*—David C Thomas
(74) *Attorney, Agent, or Firm*—Nixon Peabody LLP

(57) ABSTRACT

A method of identifying RNA ligands which bind to a target molecule by treating a first pool of RNA ligands that collectively bind more than one target under conditions effective to reduce the concentration or eliminate the presence of one or more predominate target-binding RNA ligands from the first pool of RNA ligands; amplifying the RNA ligands in the treated first pool, thereby forming a second pool of RNA ligands that is enriched in one or more non-predominate target-binding RNA ligands of the first pool but not the one or more predominate target-binding RNA ligands thereof; and identifying one or more predominate target-binding RNA ligands that are present in the second pool at a higher concentration than other target-binding RNA ligands. Oligonucleotides and kits which can be used in practicing the present invention are also disclosed, as are aptamers that bind to a heat shock factor protein and their use.

21 Claims, 10 Drawing Sheets

OTHER PUBLICATIONS

Marshall et al., "A Biopolymer by Any Other Name Would Bind as Well: A Comparison of the Ligand-binding Pockets Of Nucleic Acids and Proteins," *Structure* 5(6):729-734 (1997).

Klug et al., "In vitro and in vivo Cha racterization of Novel mRNA Motifs That Bind Special Elongation Factor SelB," *Proc. Natl. Acad. Sci. USA* 94(13):6676-6681 (1997).

Urvil et al., "Selection of RNA Aptamers That Bind Specifically to the NS3 Protease of Hepatitis C Virus," *Eur. J. Biochem.* 248(1):130-138 (1997).

Kumar et al., "Isolation of RNA Aptamers Specific to the NS3 Protein of Hepatitis C Virus From a Pool of Completely Random RNA," *Virology* 237(2):270-282 (1997).

Weiss et al., "RNA Aptamers Specifically Interact With the Prion Protein PrP," *J. Virol.* 71(11):8790-8797 (1997).

Shi et al., "Artificial Genes Expressing RNA Aptamers as Specific Protein Inhibitors in vivo," *Nucleic Acids Symposium Series* 36:194-196 (1997).

Shi et al., "A Specific RNA Hairpin Loop Structure Binds the RNA Recognition Motifs of the *Drosophila* SR Protein B52," *Mol. Cell. Biol.* 17(5):2649-2657 (1997).

Shi, "Perturbing Protein Function with RNA Aptamers," Thesis, Cornell University, University of Microfilms, Inc. (1997).

Chen et al., "Multitarget-Ribozyme Directed to Cleave at Up to Nine Highly Conserved HIV-1 env RNA Regions Inhibits HIV-1 Replication-Potential Effectiveness Against Most Presently Sequenced HIV-1 Isolates," *Nucl. Acids Res.* 20(17):4581-4589 (1992).

Shi et al., "Evolutionary Dynamics and Population Control During In Vitro Selection and Amplification With Multiple Targets," *RNA* 8:1461-1470 (2002).

* cited by examiner

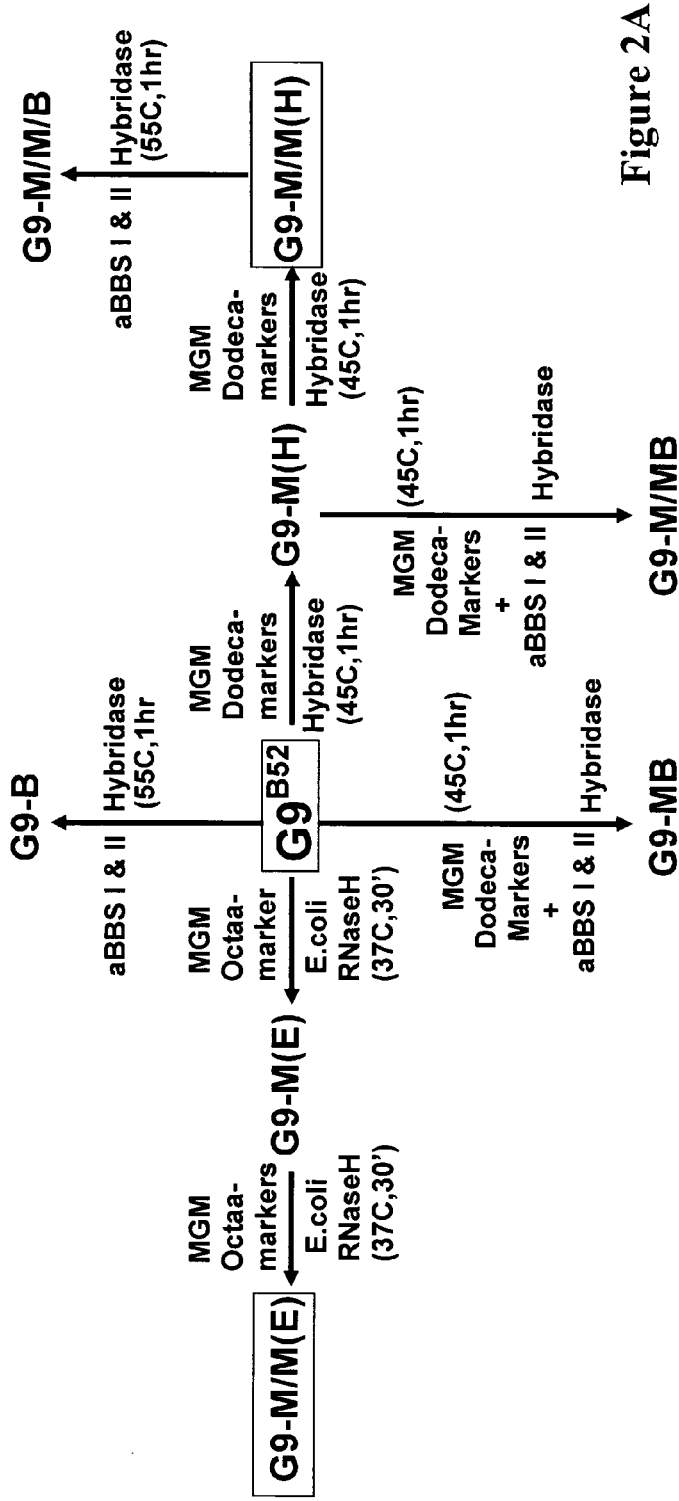
Figure 2A
Figure 2B

|  | MGM abundance | |
|---|---|---|
|  | Before treatment | After treatment |
| B52 | G9 94% (62/66) | G9-M/M(E) 45% (9/20) |
| HSF/L | G9 87.5% (7/8) | G9-M/M/M 9% (2/22) |
| HSF/H | G9 100% (1/1) | G9-M/M/M 3% (1/27) |

Figure 4

| | | | | | | |
|---|---|---|---|---|---|---|
| | 14-1 | | 14-2 | | 9a-1 | |
| HSF | - | + | - | + | - | + |
| BSA | + | - | + | - | + | - |

14-1 ATCGCGATACAAAATTAAGTTGAACGCGAGTTCTCCATCT (SEQ ID NO: 28)
14-2 AAGTAGCTAGGAGTCCTTCTCCCCTCAAAACAGAATGGGG (SEQ ID NO: 29)
9a-1 GGCAAGCTACGCGTCAAATAGCAAGCACACCGAAGACACA (SEQ ID NO: 30)

US 7,435,542 B2

EXHAUSTIVE SELECTION OF RNA APTAMERS AGAINST COMPLEX TARGETS

This application claims priority benefit of U.S. Provisional Patent Application Ser. No. 60/391,255 filed Jun. 24, 2002, which is hereby incorporated by reference in its entirety.

This invention was made in part with government support under US Public Health Service Grant GM40918. The U.S. government may have certain rights to this invention.

FIELD OF THE INVENTION

The present invention generally relates to the fields of molecular biology and genetics, and is more particularly directed to the exhaustive isolation of novel RNA ligands (aptamers) to complex molecular or super-molecular targets. The processes have applications in both basic biological research and therapeutic intervention, especially in the areas of drug discovery and functional genomics.

BACKGROUND OF THE INVENTION

Over the past decade, numerous methods that combine the power of combinatorial chemistry and high-throughput screening have been developed to generate novel ligands that are critical to both basic research and therapeutic applications. Among these methods, the adaptive molecular evolution techniques with RNA, also known as SELEX (Tuerk and Gold, "Systematic Evolution of Ligands by Exponential Enrichment: RNA Ligands to Bacteriophage T4 DNA Polymerase," *Science* 249:505-510 (1990)), is particularly powerful thanks to the unique features of the RNA molecules, which not only carry information for their own replication but also fold into well-defined shapes. The novel ligands, or aptamers (Ellington and Szostak, "In vitro Selection of RNA Molecules that Bind Specific Ligands," *Nature* 346:818-822 (1990)), generated by this SELEX process are capable of binding to a wide variety of targets with high affinity and specificity (Gold et al, "Diversity of Oligonucleotide Functions," *Ann. Rev. Biochem.* 64:763-797 (1995); Wilson and Szostak, "In vitro Selection of Functional Nucleic Acids," *Ann. Rev. Biochem.* 68:611-647 (1999)).

There has been a growing need in the drug discovery and functional genomics fields to develop methods that would yield aptamers against multiple targets in a single selection experiment. Experiments have been performed against multi-subunit enzymes (Brown and Gold, "Template Recognition by an RNA-dependent RNA Polymerase: Identification and Characterization of Two RNA Binding Sites on Qβ Replicase," *Biochemistry* 34:14765-14774 (1995); Brown and Gold, "RNA Replication by Qβ Replicase: a Working Model," *Proc. Natl. Acad. Sci. USA* 93:11558-11562 (1996)), viral particles (Pan et al, "Isolation of Virus-neutralizing RNAs from a Large Pool of Random Sequences," *Proc. Natl. Acad. Sci. USA* 92:11509-11513 (1995)), organelles (Ringquist et al, "High-affinity RNA Ligands to *Escherichia coli* Ribosomes and Ribosomal Protein SI: Comparison of Natural and Unnatural Binding Sites," *Biochemistry* 34:3640-3648 (1995)), and entire cells (Morris et al, "High Affinity Ligands from in vitro Selection: Complex Targets," *Proc. Natl. Acad. Sci. USA* 95:2902-2907 (1998)), with different degrees of success. In some cases, different families of ligands were identified for different targets in the mixture. However, these aptamers recognize the most abundant or easily recognizable target sites, which are not necessarily the most desired ones. No existing literature, i.e. none of the experiments performed so far and none of the currently available methods, offers an approach which is capable of generating different ligands to all of the targets in a mixture.

The most important step in the SELEX procedure is the partitioning step in which the target-binding species is physically separated from the non-binding species. The immobilization matrix used as partitioning device can act as an unwanted target to generate unwanted aptamers that often dominate the selected pool. Several methods are commonly in use to avoid this problem (Conrad et al, "In vitro Selection of Nucleic Acid Aptamers that Bind Proteins," *Methods in Enzymology* 267:336-367 (1996)). First, matrix-binding species may be eliminated by negative selection against the matrix, i.e., collecting the fraction not bound to the matrix. However, in early cycles, when the copy number of each clone is low, this extra handling may increase the chance of stochastic events in which a particular sequence is lost. In later rounds, when the matrix bound species becomes the dominant sequence population in a pool, this method may not be efficient enough to eliminate them. Second, since the number of binding site on the surface of the matrix is fixed, increasing the amount of the target may change the ratio of the matrix-binding species to target-binding aptamers in favor of the recovery of the target-binding aptamers in the partitioning step. But the number of binding sites on the matrix can be extremely large compared to that on the target even at its highest level, thus rendering this method ineffective. In addition, higher target amounts will also favor the isolation of ligands with lower affinity, thus decreasing the efficiency of selection. Third, alternating use of different types of matrices should theoretically eliminate molecules binding to either. This method is less effective than might be expected because the difference between the commonly used matrices is not sufficient to discriminate against common aptamers that can bind via less specific hydrophobic interactions. Because of the lack of an efficient and specific negative selection method, the background problem is still a major reason of failure during in vitro selection experiments.

SUMMARY OF THE INVENTION

A first aspect of the present invention relates to a method of identifying RNA ligands which bind to a target molecule, the method including: treating a first pool of RNA ligands that bind more than one target under conditions effective to reduce the concentration or eliminate the presence of one or more predominate target-binding RNA ligands from the first pool of RNA ligands; amplifying the RNA ligands in the treated first pool, thereby forming a second pool of RNA ligands that is enriched in one or more non-predominate target-binding RNA ligands of the first pool but not the one or more predominate target-binding RNA ligands thereof; and identifying from the second pool one or more predominate target-binding RNA ligands that are present in the second pool at a higher concentration than other target-binding RNA ligands.

A second aspect of the present invention relates to a method of reducing the concentration or eliminating the presence of unwanted target-binding species from a pool of RNA ligands, the method including: providing a pool of RNA ligands which includes both wanted and unwanted target-binding RNA ligands; identifying one or more unwanted target-binding RNA ligands; and treating the pool under conditions effective to reduce the concentration or eliminate the presence of the one or more unwanted target-binding RNA ligands from the pool of RNA ligands.

A third aspect of the present invention relates to an oligoDNA molecule that hybridizes to an RNA ligand, which binds to a partitioning matrix, and is capable of directing an RNaseH enzyme to cleave a hybrid complex formed by the oligoDNA molecule and the RNA ligand. A duplex formed between an oligoDNA molecule of the present invention and an RNA ligand that binds to a partitioning matrix is also disclosed.

A fourth aspect of the present invention relates to a kit for selecting RNA ligands which bind to one or more target molecules, the kit including: a matrix for partitioning RNA ligands that bind to one or more target molecules from RNA ligands which do not; an isolated oligoDNA molecule of the present invention; and an RNaseH enzyme.

A fifth aspect of the present invention relates to a nucleic acid aptamer that binds to a heat shock factor protein. The nucleic acid can be either DNA or RNA. A related aspect of the present invention concerns a multivalent RNA aptamer that includes two or more aptamers that bind to a heat shock factor protein.

A sixth aspect of the present invention relates to a method of modifying activity of a heat shock factor protein that includes: binding a nucleic acid aptamer of the present invention to a heat shock factor protein under conditions effective to modify the activity of the heat shock factor protein. A related aspect of the present invention concerns modifying the activity of the heat shock factor protein, which thereby modifies a stress response mediated by the heat shock factor protein.

The present invention offers a general method that allows the exhaustive isolation of novel RNA ligands (aptamers) to multiple or complex, even inseparable, molecular or supermolecular targets. This is afforded by including within general iterative selection procedures a step that decreases or eliminates any of one or more aptamers or aptamer families whose sequence information are available. Predominant RNA ligands that are selected over other RNA ligands, once identified, can be decreased or eliminated from a pool of selected aptamers to allow other aptamers to dominate the subsequent generations of the pool and be identified. Unwanted partition matrix-binding species, such as nitrocellulose filter-binding RNA ligands, can likewise be decreased or eliminated from a pool of selected aptamers.

BRIEF DESCRIPTION OF THE DRAWINGS

FIGS. 2A-B illustrates relationships between the RNA pools generated in one embodiment of the present invention. The ninth generation (G9) of three previous SELEX experiments involving the *Drosophila* B52 (FIG. 2A) or HSF (FIG. 2B) proteins as targets were used as starting materials (G9$^{B52}$, G9$^{HSF/H}$, and G9$^{HSF/L}$). These pools were treated by different combinations of Marking Oligos and RNaseH under indicated conditions. MGM is "Multi-G Motif" that binds to the nitrocellulose filter used as the partitioning matrix. BBS is "B52 Binding Sequence" that binds to the intended target protein B52. The "Octamarker" set contains equal amount of SEQ ID Nos: 5-9 as specified in the Examples infra. The "Dodecamarker" set contains equal amount of SEQ ID Nos: 10-14 as specified in the Examples infra. "aBBS I & II" are oligonucleotides (SEQ ID Nos: 16 and 17) as specified in the Examples infra. Conditions of treatments are implicitly indicated in the name of the derivatized pools. For example, G9-M/M(H) were treated twice (-M/M) to eliminate the MGM family by the Hybridase. Those pools that are cloned and sequenced are indicated by boxes encasing their names.

FIG. 4 is a table that further illustrates the efficiency of MGM restriction in three different selected pools with different intended protein targets or selected under different conditions. The results were compiled from sequencing data. The abundance of MGM before and after the restriction is shown as percentage of MGMs in sample clones sequenced. The two numbers in the parentheses indicate actual number of MGM individuals/total number of sequenced individuals.

```
MGM-I
aacguagaac caauaagggu augggaaggg uaaaaggga        39  (SEQ ID No: 1)

MGM-II
cacaacgauc aaaagaaaag ggagggccgg ggaaggguug gacaaacagg  50  (SEQ ID No: 2)

MGM-III
gcccacgacc aaaacaaagg gaaggaggga gggugcagac gaaagccagg  50  (SEQ ID No: 3)

Ctr
uacaacaucg uagcguggca acugauggcu uugccgaacu cugaa  45  (SEQ ID No: 4)
```

Figure 8A:
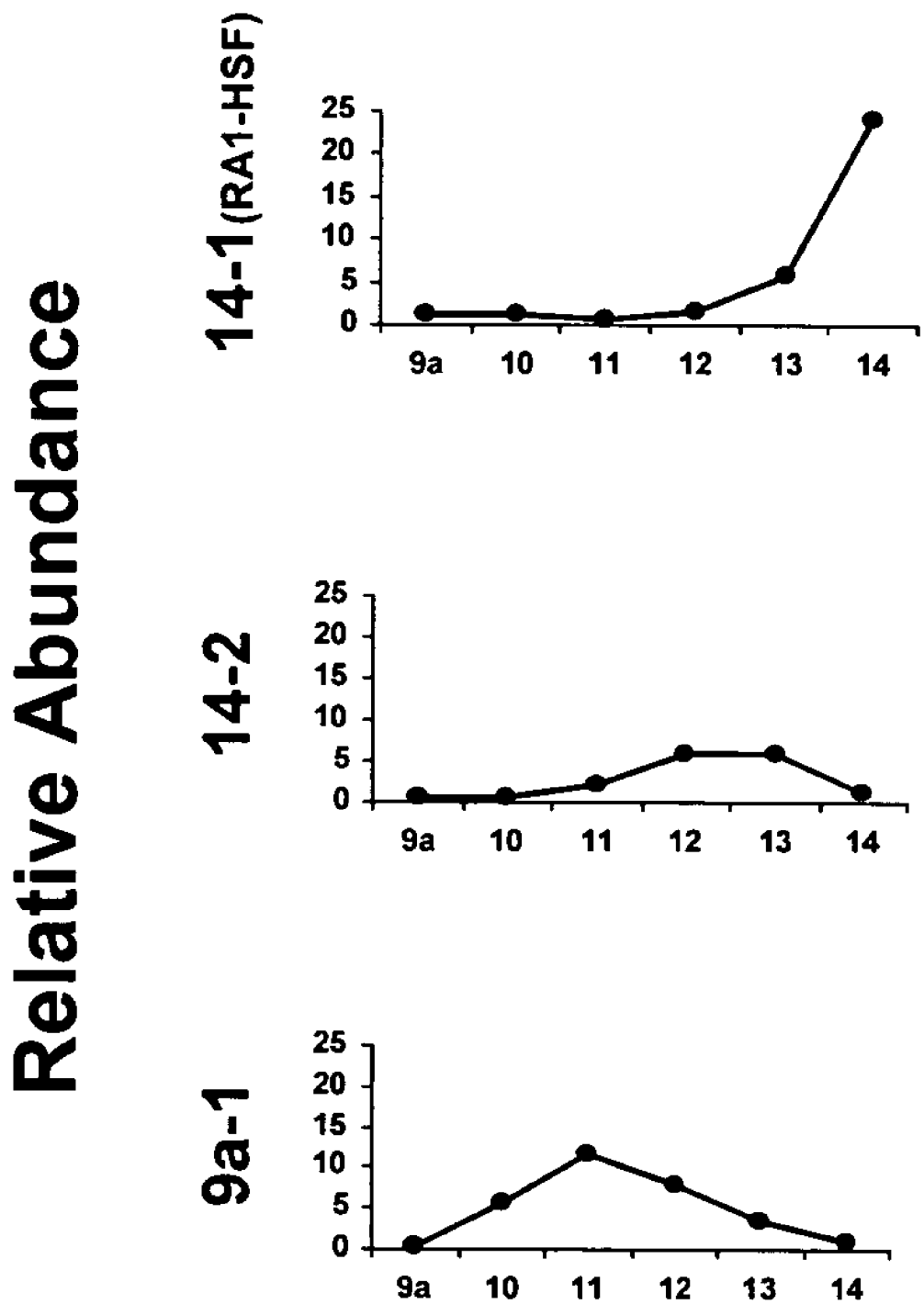
Figures 8B, 8C:
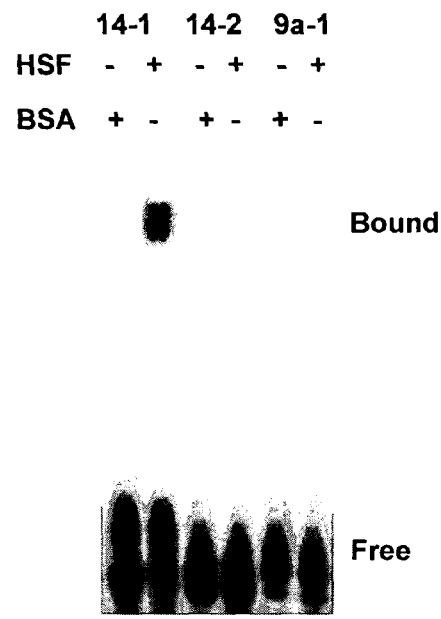

FIGS. 8A-C illustrate the correlation between the aptamers' affinity to the target and their enrichment dynamics during the second stage of selection against the *Drosophila* HSF protein. Three clones were chosen to examine because they were isolated in multiple copies, an indication of their being selected by the targets. The DNA sequences encoding the randomized regions of these RNA aptamers, #14-1 (RA1-HSF), #14-2, and #9a-1 are shown in FIG. 8C. (The full length DNA sequence, from 5' to 3', includes nt 1-25 of SEQ ID NO: 31, the sequences shown in FIG. 8C, and nt 66-90 of SEQ ID NO: 31.) Their relative abundance over time between generations G9a and G14 (FIG. 8A) shows that #14-2 and #9a-1 were out-competed by #14-1. Their fate can be explained by their relative affinity to HSF, as shown in FIG. 8B, which is an electrophoretic mobility shift assay with 100 nM of either HSF or BSA (bovine serum albumin).

Figure 9A:
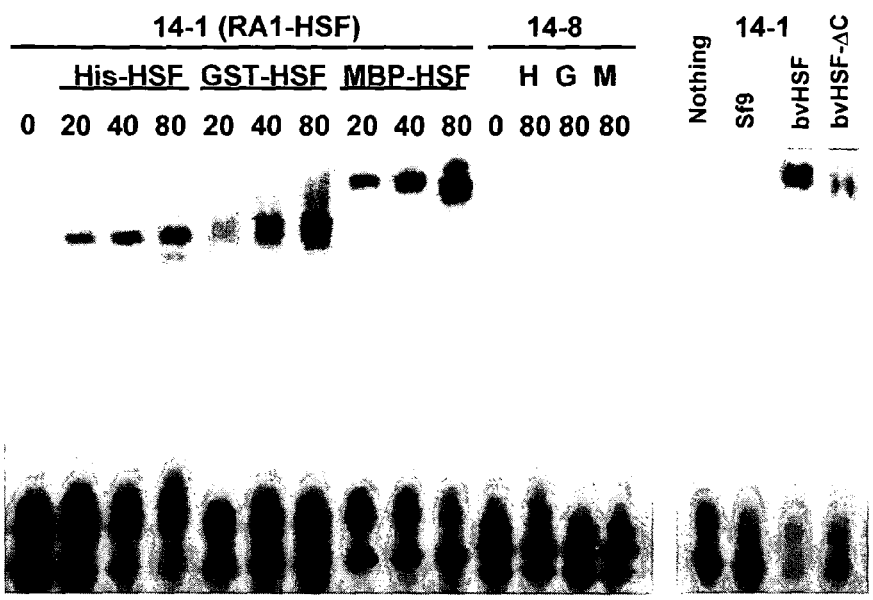
Figure 9B:
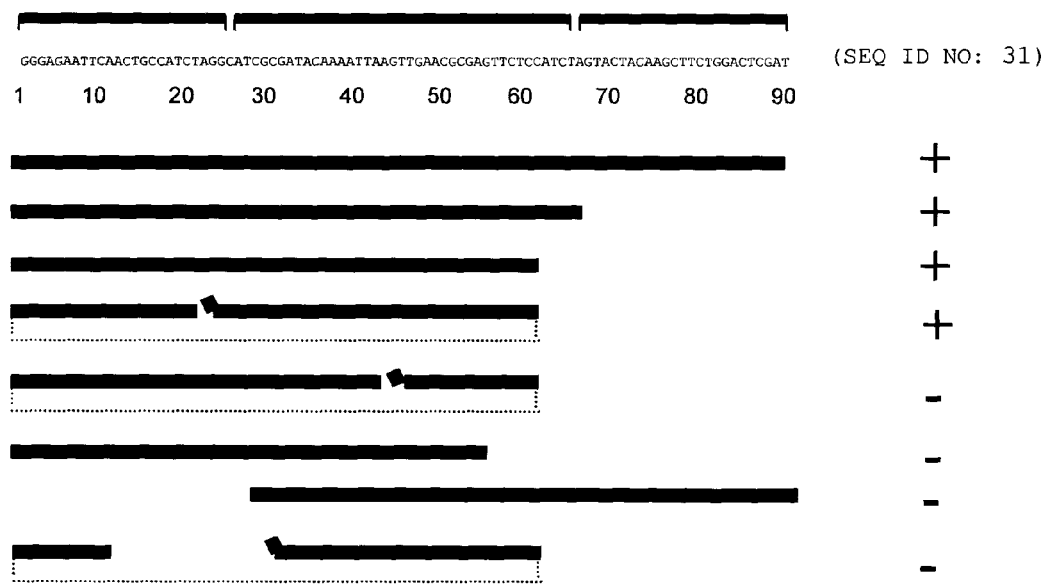

FIG. 9A illustrates the affinity of the aptamer RA1-HSF (#14-1) to different construct of the protein. The left panel shows the result with three HSF fusion constructs prepared from bacteria. Numbers indicate concentration in nanomolar. #14-8 is a negative control. The right panel shows binding of this aptamer to HSF expressed from a baculovirus vector in the Sf9 insect cells (bvHSF). The lane labeled Sf9 contains crude cell extract from this cell line without the expression vector. A truncated version of HSF (bvHSF-deltaC) was also tested for aptamer binding. FIG. 9B shows the results of deletion analyses performed to define the true aptamer moiety of RA1-HSF. The top bar above the sequence defines the 40 nt randomized region (central) and the 25 nt 5' constant region (left side) and the 25 nt 3' constant region (right side).

DETAILED DESCRIPTION OF THE INVENTION

One aspect of the present invention is a general method that allows the exhaustive isolation of novel RNA ligands (aptamers) to complex, even inseparable, molecular or super-molecular targets. The targets can be natural or synthetic small molecules, macromolecules and supramolecular assemblies, and combinations thereof. Exemplary targets can include, without limitation, nucleotides, peptides, proteins or polypeptides, protein-protein complexes, protein-nucleic acid complexes, viruses, cells, etc.

Although SELEX was traditionally intended to generate aptamers against single targets, in a formal sense all SELEX experiments contain multiple targets. Mixtures that are used as targets in SELEX experiments come in the following common forms. First, the target can be a mix of multiple distinctive molecules, where aptamers against all target molecules are desirable. The targets may be separable, but a simultaneous selection is more economical. Second, a single target molecule can contain multiple discrete binding sites on its surface, where aptamers against all sites are desirable, but separation of the different target sites is physically impossible. Third, a presumably pure target preparation may contain an unknown contaminant, which may select unwanted aptamers that come to dominate the population. Finally, even the traditional single target selection requires a partitioning matrix (e.g. filters used to collect RNA-protein complexes) that can function as an unwanted but largely inseparable target, which often selects undesired aptamers with the potential to overrun the population.

In a multi-target selection experiment, the most important issue is to ensure that different ligands to all of the targets in a mixture can be generated. The present invention affords an exhaustive approach to achieve this objective. In SELEX or other selection procedures, the step of partitioning preferentially allows those molecular species that are fit to perform certain tasks (i.e., binding to the target) to reproduce. The change of the relative concentration of a certain sequence or sequence family under competition over successive generations is determined by its growth constant, which determines the rate of self-reproduction. If the growth constant of a certain species is greater than the average growth constant due to a higher recovery in partitioning, its relative concentration will increase; otherwise, it will decay. During the progression of selection, the average growth rate will increase steadily with cycles of selection and amplification until it reaches a maximum, when the relative concentration of the one sequence (or family of sequence) having the maximal growth rate increases to one, and the relative concentrations of all other sequences decay to zero. This "extremum principle" (Eigen, "New Concepts for Dealing with the Evolution of Nucleic Acids," *Cold Spring Harbor Symposia on Quantitative Biology* 52:307-320 (1987), which is hereby incorporated by reference in its entirety) describes a behavior different from chemical equilibration. While chemical equilibration will yield definite concentration ratios determined by free energy of each species, selection eventually gives rise to only one survivor or a group of equivalently fitting survivors, regardless of whether the system as a whole grows or whether it reaches a steady state.

This outcome contradicts the aforementioned desire to isolate different ligands to multiple targets in a mixture, as only one or a very few sequence families with high relative growth rates will have the opportunity to be enriched and identified. The difference between the growth constant of different ligand families during a selection against multiple targets is determined not only by the difference in target concentration and binding affinity, but also by the difference in other unidentified factors that determine the topography of the fitness landscape of different families. All these variables (save the relative target concentration in some cases) are unknown at the onset of the experiment. To ensure that aptamers against all potential target sites are isolated, the present invention allows for adjusting of the growth constant of any aptamer clone or aptamer family based on their sequence information, without having to rely on the change of target concentration and affinity, and without interfering with the normal selection and amplification steps.

Although the present invention is not intended to be limited to any one particular selection and amplification procedure, it is convenient to discuss the present invention as it is used in a SELEX experiment with RNA. It should therefore be appreciated by those of ordinary skill in the art that the present invention also can be used in combination with, e.g., in vitro selection for enzymatic activities, in vitro selection using DNA or modified oligonucleotides, or in vitro selection with peptides.

An RNA aptamer for a protein or other kind of target usually mimics the shape of a natural ligand of the target. As the identity of a mimic is defined by the authentic, a mimic in a different chemical nature may not be as perfect as what it mimics. Although RNA is an extraordinarily versatile type of molecule, it cannot be guaranteed that an RNA ligand always exists for a binding site on a protein domain naturally occupied by a non-RNA molecule. On the other hand, multiple different RNA sequence/structure solutions may exist to fit some sites. Therefore, exhaustive selection of RNA aptamers in the sense of "one for each site" is not realistic if the sites are not defined by RNA. Nonetheless, the method described herein pursues exhaustiveness in aptamer identification in a practical sense: Every RNA ligand existing in the starting sequence pool should be isolated. Starting with a large diverse pool for every new stage may yield multiple aptamers for each binding site on the targets.

In a SELEX experiment, genetic selection is applied directly to populations of RNA molecules that possess both genotypes (a sequence) and phenotypes (a binding activity that varies according to sequence). The conventional SELEX method attempts to recapitulate the natural Darwinian evolution process, in which the selection is based on phenotype (e.g. binding capability possessed by a folded RNA) and amplification is based on genotype (base paring during PCR). While the fitness of molecules (their ability to be enriched) may be also affected by their relative efficiency of enzyme-mediated replication, this is intentionally minimized, rather than explored, in the process of the experiment in order to keep the selection pressure solely on the phenotype. The nucleotide sequence of a nucleic acid molecule, as the physical embodiment of the information encoded therein, can be used in itself as the criterion for either positive or negative selection. This feature has been explored in some molecular computation experiments to solve hard combinatorial optimization problems (Adleman, "Molecular Computation of Solutions to Combinatorial Problems," *Science* 266:1021-1024 (1994), which is hereby incorporated by reference in its entirety). But when a sequence functions as the genotype of an organism, it is normally not accessible and subject to selection; and when it acts as the genotype of an aptamer in an ideal "single target selection", it is unknown until it is enriched according to its phenotype to the point of its identification. Once the sequence of an aptamer is identified in such an experiment, it loses its value of being a selection criterion for itself, since by then the selection has achieved its practical goal and is considered finished. The present invention provides a scheme of negative selection according to genotype, which utilizes the sequence information to reduce the relative size of particular aptamer populations during the process of selection against multiple targets. More specifically, it allows the resumption of selection/amplification to identify less abundant aptamers to other targets, once an aptamer family is identified due to its high growth rate.

According to one aspect of the present invention, a method of identifying RNA ligands that bind to a target molecule is provided. This method is preferably performed as an exhaustive selection procedure to identify substantially all RNA ligands that appear in a pool of ligands and possess a particular phenotype (i.e., binding to a target).

A pool of RNA ligands that collectively bind to more than one target is prepared by first generating a library of RNA molecules, which likely includes both RNA ligands that bind at least one of one or more targets and RNA molecules that do not bind any of the targets, and then partitioning the library of RNA molecules to form a first pool of such RNA ligands according to the conventional selection and amplification procedure (e.g., SELEX). Partitioning of the RNA library is achieved by physically separating the non-target binding RNA molecules from target-binding RNA ligands using a partitioning matrix as is known in the art. Suitable partitioning matrices include, without limitation, nitrocellulose, agarose beads, Biacore sensor chip, and any insoluble substance to which a target can be fixed or retained, or combinations thereof. Matrices can be selected based on pore size or binding affinity for target molecules (i.e., including target:RNA complexes). As noted hereinafter, the partitioning matrix may itself behave as a target, allowing recovery of RNA ligands that bind to the matrix rather than a desired target molecule.

The resulting first pool of target-binding RNA ligands includes RNA ligands that bind to at least one of the one or more targets used during the selection and partitioning procedure. Individual RNA ligands may or may not bind to more than one target; but collectively the pool of RNA ligands binds to more than one target. After forming the first pool of target-binding RNA ligands, the one or more target-binding RNA ligands which predominate within the first pool (specifically, within the sample therefrom) are isolated and sequenced using conventional (i.e., preferably automated) sequencing procedures. Having identified the one or more predominate target-binding RNA ligands, it is also possible to compare sequences to identify whether a family of sequences exist that possess a consensus sequence.

Once the sequence of the one or more predominate target-binding RNA ligands has been determined, one or more oligonucleotides are designed specifically to hybridize to the one or more predominate target-binding RNA ligands or, alternatively, to the consensus sequence for a family of predominate target-binding RNA ligands. The oligonucleotides are preferably at least about 8 nucleotides in length, more preferably between about 10 and 100 nucleotides in length, most preferably between about 10 and about 40 nucleotides in length. It should be appreciated by those of ordinary skill in the art that longer or shorter oligonucleotides can be used; the oligonucleotides, however, must be specific for the predominate target-binding RNA ligands or the family thereof.

The first pool of RNA ligands is then treated to reduce the concentration or eliminate the presence of one or more predominate target-binding RNA ligands from the first pool of RNA ligands. Specifically, oligonucleotides that hybridize with the predominate target-binding RNA ligands (or a family thereof) are introduced into the first pool under suitable hybridization conditions to cause the oligonucleotides to hybridize to the one or more predominate target-binding RNA ligands, forming hybrid complexes. The hybridization conditions will likely vary depending upon the sequences of the one or more predominate target-binding RNA ligands (or family thereof) and the oligonucleotide introduced into the first pool. Exemplary hybridization conditions include, without limitation, 200 ng RNA (6 pmole) and 150 pmole marking oligonucleotides in 20 µl RNaseH buffer (50 mM Tris-Cl, pH 7.4, 100 mM NaCl, 10 mM $MgCl_2$) with pre-incubation at 72° C. for 3 minutes and incubation at 37° C. for 30 minutes. One skilled in the art will appreciate that conditions for nucleic acid hybridization, including temperature, salt, and the presence of organic solvents, are variable depending upon the size (i.e., number of nucleotides) and the G-C content of the nucleic acids involved, as well as the hybridization assay employed (See, e.g., Sambrook et al., *Molecular Cloning: A Laboratory Manual*, Cold Spring Laboratory, Cold Spring Harbor, N.Y. (1989); *Nucleic Acid Hybridization: A Practical Approach*, Haimes and Higgins, Eds., Oxford:IRL Press (1988), each of which is hereby incorporated by reference in its entirety).

After allowing a suitable period of time for hybridization to occur, a number of hybrid complexes (RNA ligand:oligonucleotide) will have formed within the treated first pool. To this mixture, an enzyme is added which recognizes the RNA hybrid complex and cleaves at least the RNA ligand of the hybrid complex or, alternatively, both strands of the hybrid complex. For example, an RNaseH enzyme is utilized in combination with oligoDNAs that hybridize to the predominate target-binding RNA ligands, cleaving the duplex-forming RNA ligands and thereby destroying the aptamer sequence of those RNA ligands. The oligoDNA is then released from the hybrid complex and is free to hybridize with other predominate target-binding RNA ligands (and thereby promote further RNaseH activity). For the size of hybridization described above by way of example (6 pmole RNA and 150 pmole oligonucleotides), 1 unit of RNaseH is added during the annealing after the sample is at 37° C. Of course, more or less enzyme can be added depending upon the size of the hybridization procedure. Thus, following hybridization and enzyme treatment, the first pool has effectively been treated (forming a treated first pool) so as to eliminate or otherwise substantially reduce the population of what was previously the one or more predominate target-binding RNA ligand.

Thereafter, the RNA ligands in the treated first pool are amplified using conventional reverse transcription amplification procedures, e.g., RT-PCR. As a result, a second pool of RNA ligands is formed. The second pool of RNA ligands is enriched in one or more non-predominate target-binding RNA ligands of the first pool but not the one or more predominate target-binding RNA ligands thereof. It is from this second pool of RNA ligands that one or more new predominate target-binding RNA ligands are identified. The one or more new predominate target-binding RNA ligands of the second pool are present at a higher concentration than other target-binding RNA ligands. Moreover, one or more new predominate target-binding RNA ligands of the second pool are different from the one or more predominate target-binding RNA ligands from the first pool. In other words, because the one or more predominate target-binding RNA ligands of the first pool were substantially reduced in population or eliminated from the treated first pool, the same target-binding RNA ligands will not predominate during successive rounds.

Subsequently, the one or more predominate target-binding RNA ligands of the second pool are identified as described above (i.e., isolated and sequenced) and then the second pool is treated in a manner similar to the above-described treatment of the first pool, thereby substantially reducing the concentration or eliminating the presence of one or more predominate target-binding RNA ligands of the second pool. Following amplification of the treated second pool, the RNA ligands therein are amplified as described above, forming a third pool that is enriched in one or more non-predominate target-binding RNA ligands of the second pool but not the one or more predominate target-binding RNA ligands thereof.

This same process is repeated for the third pool and each subsequent pool prepared thereafter: namely, identifying predominate target-binding RNA ligands, treating the pool of RNA ligands to substantially reduce the concentration or eliminate the presence of the one or more predominate target-binding RNA ligands therein, and amplifying the treated pool. Eventually, after two or more rounds of this entire process, substantially all of the non-predominate target-binding RNA ligands of the first pool will have been identified.

In addition to the foregoing, it may be desirable to remove certain RNA molecules from each pool in each round or in alternating rounds of conventional selection and amplification, depending on their population growth within successive pools of RNA ligands. Specifically, RNA ligands that bind to the partitioning matrix are undesirable and should periodically or systematically be removed from the population of RNA ligands which define each pool. To achieve this result, oligonucleotides known to hybridize with RNA ligands that bind to the partitioning matrix can simultaneously be introduced along with oligonucleotides that hybridize to the identified one or more predominate target-binding RNA ligands. The oligonucleotides preferably possess the same characteristics and properties as the oligonucleotides described above.

From the foregoing description, it should be appreciated by those of skill in the art that a predominate target-binding RNA ligand, once identified, becomes (much like the RNA ligands that bind to the partitioning matrix) operationally undesirable or unwanted. Because the sequence for such an RNA ligand is known, the sequence information is used to earmark the unwanted RNA ligands in the population and subject them to destruction using the treatments described above and demonstrated in the example hereinafter. Iterative rounds of this growth-rate reduction step will ensure that any ligand family, regardless of their initial relative growth rate, should have an opportunity to dominate the population and thus be identified in successive selection cycles.

As an alternative to working with RNA ligands, it should be appreciated by those of ordinary skill in the art that DNA ligands that bind to at least one of one or more targets can be identified in substantially the same way. Exemplary approaches for in vitro selection of DNA ligands is described for example in Bock et al., "Selection of Single Stranded DNA Molecules That Bind and Inhibit Human Thrombin," *Nature* 355:564-66 (1992); and Huizenga et al., "A DNA Aptamer That Binds Adenosine and ATP," *Biochemistry* 34:656-65 (1995), each of which is hereby incorporated by reference in its entirety. Thus, the library of DNA molecules is exposed to one or more target molecules. Thereafter, either a partitioned or an unpartitioned library of DNA ligands is transcribed to form a library of RNA molecules as described (which itself is either partitioned or unpartitioned). The transcription can be achieved by using, e.g., PCR primers for transcription that include a T7 promoter. Once the library of RNA molecules is obtained, the library can be treated to substantially reduce the concentration or eliminate the presence of one or more predominate target-binding RNA ligands. The treated pool of RNA can then be converted back into DNA using any suitable reverse transcription procedure (i.e., RT-PCR).

Regardless of the approach, once the exhaustive selection of RNA ligands has been completed or, rather, once any one individual RNA ligand has been obtained, the RNA ligands can then be used to develop multivalent RNA aptamers (as well as constructs encoding the same), as described in U.S. Pat. No. 6,458,559 to Shi et al., which is hereby incorporated by reference in its entirety.

Figure 1:
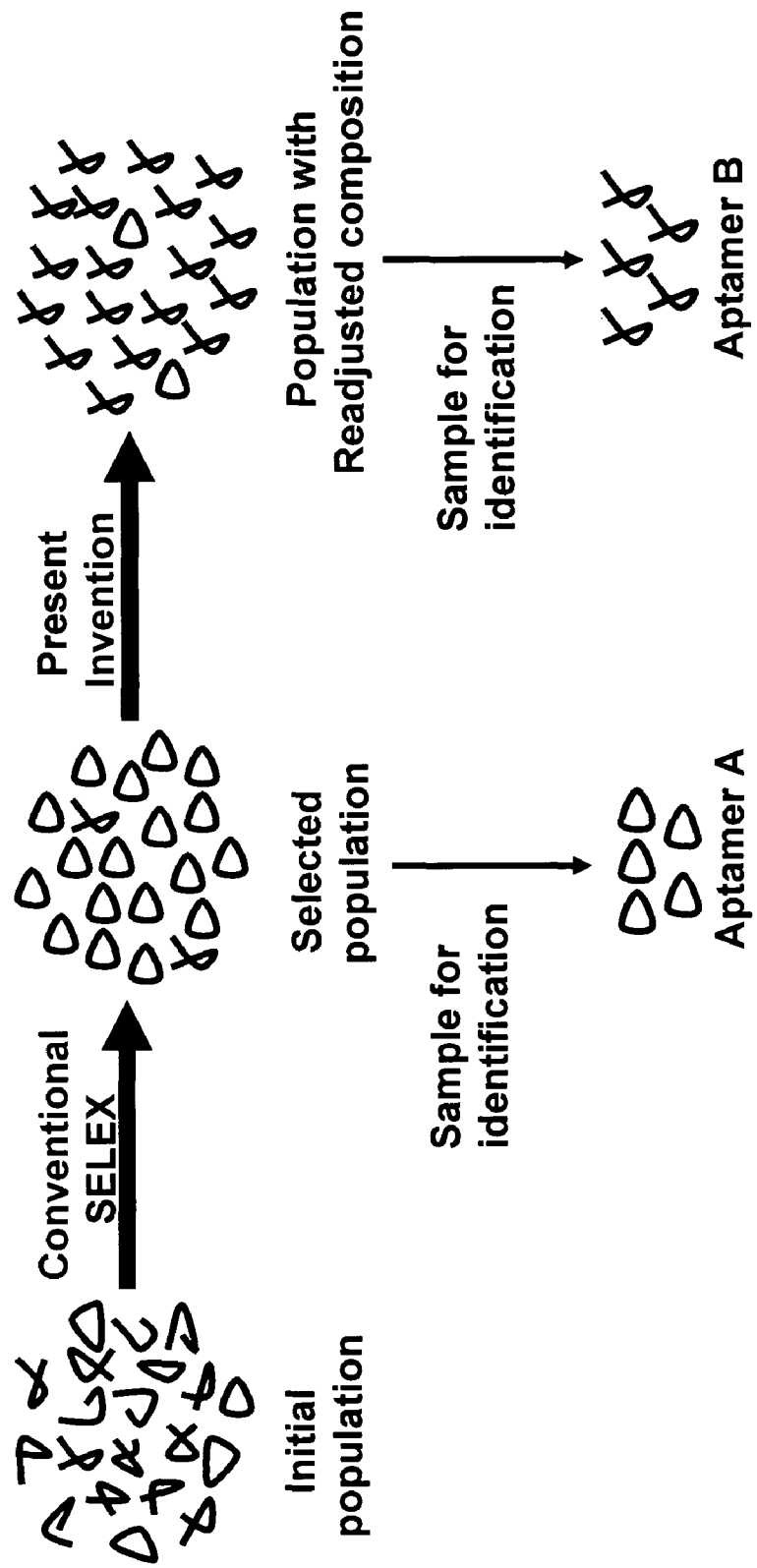
FIG. 1 is a schematic diagram depicting the simplest case of exhaustive aptamer selection with two targets. It shows the relationship between the present invention and the SELEX method. Conventional SELEX yields only Aptamer A, which may or may not be desired. The present invention, of which the SELEX method is a specific example, allows both aptamer families to be identified. As the scheme depicted here can be used iteratively, the present invention also ensures the exhaustive isolation of aptamer families in experiments involving more than two targets.

For purposes of illustration, the simplest case of an exhaustive selection against two targets is shown in FIG. 1. This scheme can be extended to more complicated ones along two directions. First, the conventional SELEX and the method of the present invention do not have to be used in a chronologically discrete manner as depicted in FIG. 1. Rather, a population restriction step can be incorporated into any or all SELEX cycles. Second, more than two targets, and in turn, more than two aptamer families can be included in a selection experiment. And, a single restriction step can treat more than one family. While sometimes more than one family of aptamers may be identified by the conventional SELEX, it only ensures the isolation of one aptamer family in a process governed by the "extremum principle" stated above. The present invention thus implements a "multiple extrema" process, in distinct steps, to ensure the exhaustive isolation of all aptamer families against a mixture of targets. Therefore, the present invention is not merely an improvement of the conventional SELEX method. Rather, it is a more general method that is applicable for use in conjunction with most any amplification and selection protocol. Use of the present invention with the conventional SELEX method, such as that described by U.S. Pat. No. 5,270,163 to Gold et al., which is hereby incorporated by reference in its entirety, is only a single embodiment.

Another aspect of the present invention is a general method that reduces the concentration or eliminates the presence of unwanted RNA ligands (i.e., previously identified RNA ligands, especially matrix-binding RNA ligands) which may otherwise thwart the isolation of desired aptamers against intended targets from a pool or population of RNA ligands. Basically, this procedure is carried out as described above, by identifying one or more unwanted target-binding RNA ligands present in a pool of RNA ligands, which includes both wanted and unwanted target-binding RNA ligands, and then treating the pool under conditions effective to reduce the concentration or eliminate the presence of the one or more unwanted target-binding RNA ligands from the pool of RNA ligands. Oligonucleotide and enzyme treatment for destruction of hybridization complexes is employed, as described above in the exhaustive selection procedure of the present invention.

A selection cycle can be conceptually divided into three steps: selection, partitioning, and amplification (Irvine et al, "SELEXION: Systematic Evolution of Ligands by Exponential Enrichment with Integrated Optimization by Non-linear Analysis," *J. Mol. Biol.* 222:739-761 (1991), which is hereby incorporated by reference in its entirety). This simplistic representation treats the selection step as an equilibrium binding process with the intended target(s). However, during selection the partitioning matrix, which is not an intended target and not necessarily at equilibrium with the aptamer candidates, is also exposed to the entire candidate pool. Binding of certain candidates to the matrix may occur, not necessarily (but nonetheless possibly) during the designated binding step, but definitely during the partitioning step that follows it. As the candidates bound to the partitioning matrix are co-partitioned with those bound to the explicitly designated target(s), the matrix acts as a de-facto target in actual experiments. RNA species selected by their interaction with the partitioning matrix are usually not desired and regarded as "background". The large number of potential binding sites on the matrix present during the partitioning step and the high partitioning efficiency of species bound to the matrix often result in the dominance of the selected pools by such unwanted species. Without effective negative selection, this may severely thwart the isolation of aptamers against the intended targets. The sequence directed RNA restriction method presented here provides an effective approach to the solution of this problem. With this method, the negative selection can be performed against genotype in addition to phenotype, thus making the negative selections collectively more efficient and specific.

Yet another aspect of the present invention is a method that specifically eliminates the unwanted filter-binding RNA generated when nitrocellulose filter is used as the partitioning device in a selection/amplification experiment. When the target in a selection experiment is a protein, a nitrocellulose filter is the popular partitioning matrix because it generally binds proteins and protein complexes but not nucleic acids (Yarus and Berg, "On the Properties and Utility of a Membrane Filter Assay in the Study of Isoleucyl-tRNA Synthetase," *Analytical Biochemistry* 35:450-465 (1970), and Yarus, "Adsorbent Filters: a New Technique for Microexperimentation on Nucleic Acid," *Analytical Biochemistry* 70:346-353 (1976), each of which is hereby incorporated by reference in its entirety). However, as shown in the accompanying Examples infra, this matrix can be a major reason behind the failure of selection experiments. The present invention provides specific reagents and schemes to solve this particular instance of the "background problem". First, when the filter-binding sequence family is identified, enzymatic treatment with RNaseH is the most effective method to get rid of those for which a marking oligonucleotide of sufficient length can be designed. Second, after removing the majority covered by a reasonably representative set of marking oligonucleotides, the remaining species can be more effectively eliminated by conventional negative selection against phenotype, i.e., filter binding. Third, since this family's affinity to the filter is dramatically compromised in the absence of potassium ion, alternative use of potassium and sodium in the binding buffer is another choice during selection when physiological conditions need to be mimicked.

A further aspect of the present invention relates to one or more kits which can be used for selecting RNA ligands that bind to one or more target molecules and, in particular, for selective removal of RNA ligands that bind to a partitioning matrix. The kits include a matrix for partitioning RNA ligands that bind to one or more target molecules from RNA ligands which do not, one or more oligoDNA molecules of the present invention (as described above), and a suitable enzyme (e.g., RNaseH) that cleaves a hybrid complex formed by the oligonucleotide molecule and RNA ligands that bind to the matrix. The kits can be used alone or in combination with other components useful in practicing the present invention. For example, the kits can also include reagents for amplifying RNA ligands (e.g., reverse transcriptase, DNA and/or RNA polymerases, dNTPs, rNTPs, etc.).

As one embodiment of the present invention, a previously performed selection experiment was extended. The prior selection experiment yielded two families of RNA aptamers, one being dominant over the other, against two disparate targets: the intended target protein and the partitioning matrix. This previous work is described in U.S. Pat. No.

6,458,559 to Shi et al., which is hereby incorporated by reference in its entirety. By applying the population restriction method of the present invention, the relative size of these aptamer sub-populations in the selected pool was adjusted. Since the previously dominant sub-population contained RNA species that bind to nitrocellulose filters, which is the most widely used partitioning matrix for protein targets, this also yielded a specific method and a group of specific reagents for decreasing this common background in these experiments. This method was tested on two other selection experiments involving a different target.

In isolating RNA aptamers against the *Drosophila* splicing factor B52, the original pool was carried through nine cycles of selection and amplification with filter binding as the partitioning device (Shi et al, "A Specific RNA Hairpin Loop Structure Binds the RNA Recognition Motifs of the *Drosophila* SR Protein B52," *Mol. Cell. Biol.* 17:1649-1657 (1997), which is hereby incorporated by reference in its entirety). No negative selection against the filter was performed until the last cycle, in which the recovered bound RNAs were passed through the same kind of filter before being amplified by RT-PCR. After cloning the pool of the ninth generation (G9), the binding capability of the individual clones to the B52 protein was tested in a band shift assay. Among the 66 clones tested in one sampling, only 4 showed high-affinity specific binding. Their sequence contained a consensus that was later identified as the B52 Binding Sequence (BBS). Sequences of the clones that were not able to bind B52 belong to a family whose members contain around four (usually 3-5) G-triplets. In most cases these G-triplets occur within a sequence segment 25-nt in length, and there is often an A preceding the G-triplet. Sequences meeting these criteria were termed "Multi-G Motif (MGM)". A filter-binding assay revealed dramatic increase of filter binding capability of the G9 pool over the unselected pool G0, and the same assay with individual MGM clones confirmed their contribution to the pool's increased average filter-binding affinity. These results indicated that two families of aptamers were selected by two different targets in this selection experiment.

With the identified activities and corresponding consensus sequences of these two families, a detailed retrospective analysis was performed on the evolving RNA populations to study the relationship between the selected RNAs and the random sequence pool from which they arise (Shi et al, "Evolutionary Dynamics and Population Control During in vitro Selection and Amplification with Multiple Targets," *RNA.* 8:1461-1470 (2002), which is hereby incorporated by reference in its entirety). The data obtained in these studies on population dynamics indicate that this selection experiment is a valuable model system for SELEX against two or more co-existing targets. Moreover, BBS and MGM represent both extremes of the consensus aptamer sequence in terms of their length and degree of homology. Successful ablation of both from the pool, either successively or simultaneously, demonstrated the efficiency and versatility of the method presented here.

Using the exhaustive selection procedure of the present invention to identify RNA aptamers of the *Drosophila* heat shock factor protein, three RNA aptamers were identified.

```
The DNA molecules (i.e., reverse transcript) of the three RNA
   aptamers are the DNA moleculse of SEQ ID Nos: 31 (14-1),
        32 (14-2), and 33 (9a-1) as set forth below:
14-1
gggagaattc aactgccatc taggcatcgc gatacaaaat taagttgaac gcgagttctc   60
catctagtac tacaagcttc tggactcgat                                    90

14-2
gggagaattc aactgccatc taggcaagta gctaggagtc cttctcccct caaaacagaa   60
tggggagtac tacaagcttc tggactcgat                                    90

9a-1
gggagaattc aactgccatc taggcggcaa gctacgcgtc aaatagcaag cacaccgaag   60
acacaagtac tacaagcttc tggactcgat                                    90

The corresponding RNA aptamers encoded by the DNA molecules of
         SEQ ID Nos: 31, 32, and 33 are set forth below as
               SEQ ID Nos: 34, 35, and 36, respectively:
14-1
gggagaauuc aacugccauc uaggcaucgc gauacaaaau uaaguugaac gcgaguucuc   60
caucuaguac uacaagcuuc uggacucgau                                    90

14-2
gggagaauuc aacugccauc uaggcaagua gcuaggaguc cuucucsccu caaaacagaa   60
uggggaguac uacaagcuuc uggacucgau                                    90

9a-1
gggagaauuc aacugccauc uaggcggcaa gcuacgcguc aaauagcaag cacaccgaag   60
acacaaguac uacaagcuuc uggacucgau                                    90
```

In the DNA molecules of SEQ ID Nos: 31-33 and the RNA molecules of SEQ ID Nos: 34-36, nt 1-25 and nt 66-90 represent conserved regions, whereas nt 26-65 in each of the above-identified sequences represents a variable region that was selected during the in vitro selection procedure performed in accordance with the present invention and described in Examples 3 and 6 infra.

The target bound by the DNA molecules of SEQ ID Nos: 31-33 and the RNA molecules of SEQ ID Nos: 34-36 are heat shock factors. Heat shock factors regulate the activation of heat shock gene transcription by binding to specific promoter elements (Wu, "Heat Shock Transcription Factors: Structure and Regulation", *Ann. Rev. Cell Dev. Biol.* 11:441-469 (1995), which is hereby incorporated by reference in its entirety). Upon heat treatments, HSF forms homotrimers that bind to specific DNA sequences called heat shock elements (HSEs). The HSF senses and integrates signals from extracellular and intracellular environments and regulates the expression of heat shock genes whose products are chaperones that help proteins maintain stable folded conformations. Because heat shock factors are highly conserved proteins, the DNA ligands and RNA ligands that bind to the *Drosophila* heat shock factor proteins may also bind to vertebrate and, more specifically, mammalian heat shock factor proteins.

Thus, a further aspect of the present invention relates to a method of modifying activity of a heat shock factor protein and a method of modifying a stress response mediated by a heat shock factor protein. These methods include the step of binding the RNA aptamer of the present invention to a heat shock factor protein under conditions effective to modify the activity of the heat shock factor protein, thereby modifying a stress response mediated by the heat shock factor protein. In particular, by modifying the activity of the heat shock factor protein, it is possible to modify the level of transcription of genes under regulatory control of heat shock elements.

EXAMPLES

The following examples are provided to illustrate embodiment of the present invention. But they are by no means intended to limit its scope.

Materials & Methods

The materials and methods described below are applicable for all of the following examples.

Oligonucleotides:

The oligonucleotides used as "markers" in the RNA restriction treatment and probes in the Southern blot analysis are listed below.

```
G6A2
cccttccc                                     8  (SEQ ID No: 5)

A2G6
ccctccct                                     8  (SEQ ID No: 6)

A3G5
ccctcctt                                     8  (SEQ ID No: 7)

TAG6
cccctcca                                     8  (SEQ ID No: 8)

CTG6
cccacccg                                     8  (SEQ ID No: 9)

G6A2N4
nncccttccc nn                               12  (SEQ ID No: 10, where N = A + T + G + C)

A2G6N4
nnccctccct nn                               12  (SEQ ID No: 11, where N = A + T + G + C)

A3G5N4
nnccctcctt nn                               12  (SEQ ID No: 12, where N = A + T + G + C)

TAG6N4
nncccctcca nn                               12  (SEQ ID No: 13, where N = A + T + G + C)

CTG6N4
nncccacccg nn                               12  (SEQ ID No: 14, where N = A + T + G + C)

NCW13
nncccwwwcc cnn                              13  (SEQ ID No: 15, where W = A + T and N = A + T + G + C)

Anti-BBS I
cggtcgcctg gttgacc                          17  (SEQ ID No: 16)

Anti-BBS II
ctgtcgccag gttgatc                          17  (SEQ ID No: 17)

ForT7#2
gtaatacgac tcactatagg gagaattcaa ctgccatcta 40  (SEQ ID No: 18)
```

The individual MGM species and a control RNA with random sequence were prepared by in vitro transcription (see below) from templates made from the following oligonucleotides:

```
EDA45T7FOR
gtaatacgac tcactatagg ctacaacatc gtagcgtgg          37  (SEQ ID No: 19)

EDA45COMP
ttcagagttc ggcaaagcca tcagttgcca cgctacgatg ttgta   45  (SEQ ID No: 20)

MGM40T7FOR
gtaatacgac tcactatagg caacgtagaa ccaataag           38  (SEQ ID No: 21)
```

```
                                    -continued
MGM40COMP
tccctttac ccttcccata cccttattgg ttctacgttg       40  (SEQ ID No: 22)

MGM50IT7FOR
gtaatacgac tcactatagg cacaacgatc aaaagaa         37  (SEQ ID No: 23)

MGM50ICOMP
cctgtttgtc caacccttcc ccggccctcc cttttctttt gatcgttgtg 50  (SEQ ID No: 24)

MGM50IIT7FOR
gtaatacgac tcactatagg gcccacgacc aaaacaa         37  (SEQ ID No: 25)

MGM50IICOMP
cctggctttc gtctgcaccc tccctccttc cctttgtttt ggtcgtggg  49  (SEQ ID No: 26)

RA1-HSF, randomized region in the isolated clone
atcgcgatac aaaattaagt tgaacgcgag ttctccatct       40  (SEQ ID No: 27)
All oligonucleotides were synthesized at the 50 nmole scale by Operon Inc.
(Alameda, CA).
```

RNA Restriction Treatment:

The RNA was prepared using the T7-MAGAshortscript™ in vitro transcription kit (Ambion, Inc., Austin, Tex.) according to the manufacturer's instructions. The *E. coli* RNaseH and the thermostable Hybridase™ were purchased from Epicentre Inc. (Madison, Wis.). In the RNaseH reaction, for each unit of RNaseH, 200 ng RNA (6 pmol) and 150 (30×5) pmol marking oligonucleotides were used in 20 µl RNaseH buffer (50 mM Tris-Cl, pH 7.4, 100 mM NaCl, 10 mM $MgCl_2$). The reaction mix was preincubated at 72° C. for 3 minutes before adding the enzyme and transferring to a lower temperature specified by the type of RNaseH and the Tm of the marking oligo(s). When the *E. coli* RNaseH was used, the reaction was always held at 37° C. for 30 minutes and then stopped by addition of 10 mM EDTA. When the Hybridase™ was used, the reaction was held for one hour at a temperature 2-3 degrees below the Tm of the marking oligo. For example, 45° C. for the dodecamarkers (SEQ ID Nos: 10-14); 55° C. for the anti-BBS I and II (SEQ ID Nos: 16 and 17). When multiple oligonucleotides were included in a single reaction, the lowest Tm was used to determine this temperature. The treated pool can be amplified by RT-PCR and submitted to additional selection if needed.

To examine the effect of this restriction treatment on the entire pool, a small amount (about 20-50 fmole) of radiolabeled tracer made from transcription with the same template preparation was included in the reaction, and a fraction of the reaction mix was then run on a 8% polyacrylamide, 7 M urea gel. The radiolabeled tracer was made with [$\alpha$-$^{32}$P] UTP (NEN Life Science Products, Boston, Mass.) using the T7-MAXIscript™ in vitro transcription kit (Ambion, Inc., Austin, Tex.) according to the manufacturer's instructions. The radioactive bands on the gel were visualized by a phosphoimiger. The effect of this restriction treatment can also be assessed from the decrease of the relative abundance of the sequence family under restriction, using Southern dot blot analysis (see below). Finally, a representative sample of the pool can be cloned and sequenced to show the composition of a treated pool. The PCR products were directly cloned into the pSTBlue™-1 blunt vector using the Perfect Blunt Cloning Kit from Novagen Inc. (Madison, Wis.) according to the manufacturer's instructions. DNA sequencing was performed using the Perkin Elmer/Applied Biosystems Division Automated DNA Sequencer with BIG Dye™ Terminator chemistry and AmpliTaq-FS™ DNA polymerase by the DNA sequencing facility of the BioResource Center at Cornell University (Ithaca, N.Y.).

Southern Dot Blot Analysis:

For each DNA pool representing a generation during the selection, about 20-40 ng (0.3-0.6 pmole) sample in 2 µl were prepared in 1×SSC. Each DNA sample was denatured at 100° C. for 10 min, chilled to 0° C. quickly and kept at 0° C. for more than 5 min before being applied onto a piece of Hybond-XL membrane (Amersham Pharmacia Biotech UK Ltd., Buckinghamshire, UK). The DNA was fixed to the membrane by baking at 80° C. for 2 hours and UV cross-linking at 0.12 $J/cm^2$, 254 nm.

To prepare the probes, 20 pmole oligonucleotides (listed above) were labeled with T4 polynucleotide kinase (New England Biolabs, Inc., Beverly, Mass.) in 20 µl 1×PNK buffer at the presence of 60 µCi [$\gamma$-$^{32}$P] ATP (10,000 Ci/mmole, NEN Life Science Products, Boston, Mass.) according to manufacturer's instruction. Reactions were kept at 37° C. for 1 hour, then stopped by adding 0.5 mM EDTA (pH 8.0) to final concentration of 5 mM and heating to 65° C. for 20 min. When detecting the constant region of the pool, 300 pmole cold probe (SEQ ID No: 18) was added to the [$\gamma$-$^{32}$P] labeled probe.

The membrane was pre-hybridized for 30 min in 5×SSC/5× Denhardt's solution/0.5% SDS, before the probe was added. Hybridization was carried at 37° C. overnight (i.e., from about 12 to about 18 hours). The membrane was washed three times, each in 0.1×SSC/0.2% SDS at room temperature for 10 min. The signals on the membrane were collected by exposing to a phosphoimage screen, and quantified using ImagineQuant software (Molecular dynamics Inc. Sunnyvale, Calif.).

To reuse the membrane, the probes were stripped off by adding 100 ml boiling 0.1% SDS to the membrane and cooling gradually to room temperature.

Filter Binding Assay:

The templates for T7 transcription to produce individual MGMs and a control RNA were prepared using reciprocal primer extension with the T7FOR and COMP oligo pairs listed above (SEQ ID Nos: 19-26) during a single cycle PCR reaction. Each 100 µl primer extension reaction contains 40 pmole of each primer and yielded about 1 µg product. RNA was synthesized using the T7-MEGAshortScript™ in vitro transcription kit according to the manufacturer's instructions. The [$\alpha$-$^{32}$P] UTP incorporated RNA was prepared using the MAXIscript™ in vitro transcription kit according to the manufacturer's instructions. The labeled RNA was used as a tracer and mixed with the cold RNA at the ratio of 1:400~1:600. Different amounts of RNA were normalized into 20 µl of 1× Binding Buffer (50 mM Tris-HCl, pH 7.6, 0.5 mM $MgCl_2$, 150 mM salt-KCl, NaCl, or LiCl as indicated) to final concentrations in the range of 10-1000 nM. Each 2011 RNA preparation also contained 1 μg of yeast tRNA as a non-specific competitor. The RNA preparations were incubated at 80° C. for 5 min and then cooled down to the ambient temperature and kept there for 30 min before loading to the filter.

The setting of the filter-binding assay was modified from that of Wong and Lohman ("A Double-filter Method for Nitrocellulose-filter Binding: Application to Protein-nucleic Acid Interactions," *Proc. Natl. Acad. Sci. USA* 90:5428-5432 (1993), which is hereby incorporated by reference in its entirety). The BA-S85 NC membrane and NA45 DEAE membrane were purchased from Schleicher & Schuell Inc. (Keene, N.H.) and the GeneScreen Plus™ hybridization transfer membrane was obtained from NEN Life Science Products (Boston, Mass.). The membranes were first equilibrated with the proper 1× Binding Buffer. A 24-well slot-blot apparatus was assembled with the positively charged DEAE or hybridization membrane at the bottom and the NC membrane on the top. The vacuum was adjusted such that the flow rate was about 100 μl/min. 4-6 samples were applied to the wells each time. For each sample, the well was first flushed with 100 μl of 1× Binding Buffer, followed immediately by the application of the RNA sample, and washed with another 100 μl of 1× Binding Buffer immediately thereafter. With the vacuum on, the apparatus was disassembled and the membranes were air-dried before exposure to a phosphoimage screen.

The signals of each sample on the NC and the positively charged membrane were quantified using the ImageQuant software. The fraction of RNA retained on the NC membrane (using the sum of signals on both membranes as total) was calculated and plotted.

Partitioning by Electrophoretic Mobility Shift Assay:

A trace amount of radioactive RNA from the same RNA pool was included in binding reactions. The binding reaction mixtures were set at 4° C. for 5-10 minutes before being loaded onto a 2.5% agarose gel in ¼ TBE buffer, which was run at 4° C. The protein-bound RNA contained in the shifted band was visualized by autoradiography, retrieved, extracted, and amplified.

Example 1

MGM Restriction on the B52 Selected G9 Pool

To utilize the RNaseH activity for the purpose of selectively eliminating an RNA sequence family, several issues needed to be addressed before the procedure could be applied to a heterogeneous sequence pool. The marking oligonucleotide has a minimal required length for it to anneal to the target sequence and be recognized by the enzyme. This length may exceed the length of the consecutive consensus sequence of the aptamer to be eliminated. In order not to affect any other sequence in the pool, the fidelity of hybridization must be ensured. Longer oligonucleotides carry more information and thus are more specific if the reaction is carried out at or near its melting temperature. Therefore an RNaseH that is stable over a wide range of temperature is desirable. These conditions were tested on three single representative MGM sequences, with a random sequence as control, before extending this method to the sequence pools. Marking oligonucleotides from 6 to 21 nucleotides in length were tested with the *E. coli* RNaseH at 37° C. or a thermostable RNaseH (Hybridase) at 45° C. *E. coli* RNaseH is more efficient but less specific than the Hybridase. A marking oligonucleotide at least 8-nt in length is needed in a reaction with *E. coli* RNaseH at 37° C. For the Hybridase at 45° C. the oligonucleotide should be 12-nt or longer.

Since different sequences may give rise to common three-dimensional structures by positioning key functional groups in similar spatial orientations, the related sequences in an aptamer family may display different degrees of homology. Nonetheless, the number and identity of nucleotides in regions that are functionally important usually show high degree of homology. The G-triplets in a MGM may fall into this category. Variations, including deletions and insertions, usually occur in regions serving topological roles. Presumably this is the case of the spacers between the G-triplets. Multiple sequence alignment of MGM family revealed two challenges to test the limit of the method being developed. First, because the spacer between the G-triplets varies in both nucleotide number and identity, the consecutive consensus of the family is no more than 3-4 nucleotides in length. A degenerate population of oligonucleotides with a single G-triplet in the middle would contain little information to specify a family member; therefore, longer oligonucleotides, longer than or equal to 8 nucleotides, need to be designed in the attempt to cover the entire family or its majority. Second, poor sequence similarity among the family members necessitated a set of representative marking oligonucleotides, rather than one oligonucleotide only. This set would hybridize to overlapping subgroups of the family, which would result in high degree of imperfect hybridization during the "earmarking" step for the RNaseH treatment, thus decreasing its efficiency.

Based on their frequency in the MGM family, a group of five octamers (SEQ ID Nos: 5-9) was chosen, each covering two adjacent G-triplets separated by one or two other nucleotides (the average spacer is three nucleotides in length), in the hope that this imperfectly representative set may cover the majority of the family. These were used in treatment by the *E. coli* RNaseH. For the Hybridase, a set of dodecamers was prepared by appending two degenerate positions on each end (SEQ ID Nos: 10-14). Repeated annealing and RNaseH treatments were performed to address the problem of imperfect hybridization.

Figure 3A:
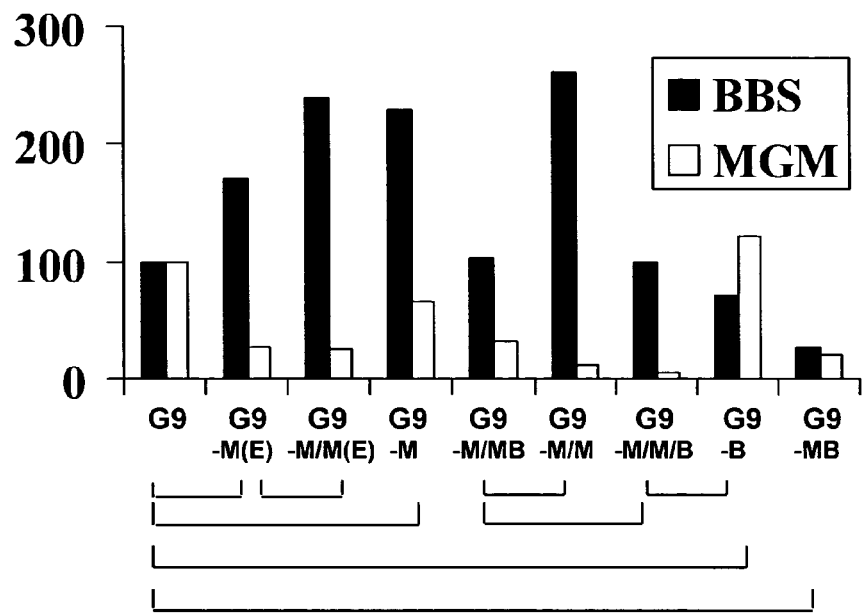
FIG. 3A is a graph that illustrates the efficiency of the RNA restriction treatment. The relative abundance of both BBS and MGM in pools treated by different combinations of Marking Oligos and RNaseH under different conditions is shown. The abundance of the aptamers in the pools (in the form of DNA) was determined by the densitometric data of Southern dot blot analysis using oligonucleotides with family consensus sequences as probes. The abundance of both aptamer families in the untreated G9$^{B52}$ pool was set as 100. The actual ratio of BBS to MGM in this untreated pool is about 1:10. To assess the effect of each treatment, the relative abundance of a family before and after the treatment (the pairwise connections below the graph) should be compared. Except for those indicated by "(E)", all other treatments were performed using the Hybridase.
Figure 3B:
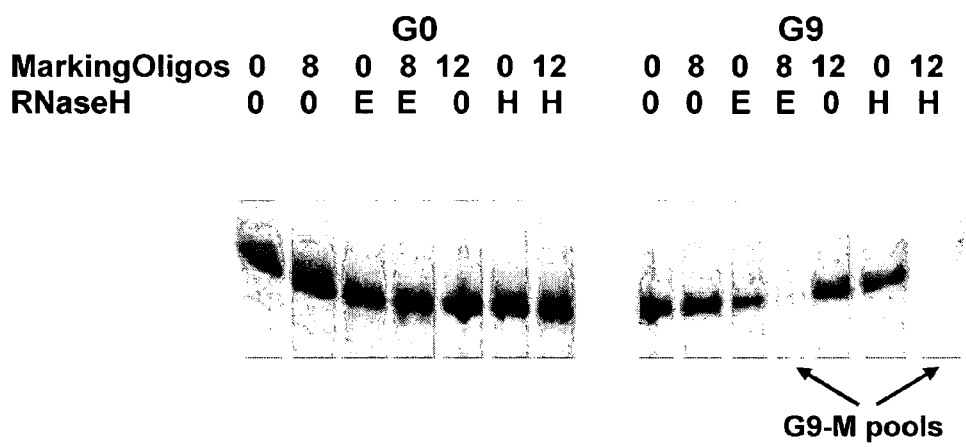
FIG. 3B illustrates the effects of MGM restriction treatment, which resulted in a decrease in the size of the MGM-dominated G9 pool. The G9 pool and the unselected G0 pool were treated with MGM marking oligos and RNaseH. "8" and "12" indicate the "Octamarkers" and "Dodecamarkers", respectively; "0" indicates controls without markers added. "E" and "H" indicate the *E. coli* RNaseH and the Hybridase, respectively.

With the "octamarker set" (SEQ ID Nos: 5-9) or the "dodecamarker set" (SEQ ID Nos: 10-14), RNA restriction treatments with RNaseH were performed on the unselected G0 pool and the selected $G9^{B52}$ pool using the optimal conditions identified with single MGM clones. Each marker set contains equal molar amount of the five oligonucleotides. A significant decrease in population size was observed in the MGM-dominated G9 but not G0 (FIG. 3B). This result is confirmed by comparing the amount of amplified RNA after the treatment by quantitative RT-PCR. Once treated, the selected pool became much more resistant to a second treatment. Family-specific probing revealed a decrease in the relative abundance of MGMs and a correlated increase in the relative abundance of BBSs after the treatments (FIGS. 3A-B). After two consecutive restriction treatments, pools G9-M/M(E) and G9-M/M(H) were cloned. (The nomenclature indicates that they were treated twice (-M/M) to eliminate the MGM family by either *E. coli* RNaseH or the Hybridase, and the relationship between all pools derived from the B52 G9 is depicted in FIGS. 2A-B) In both pools, the sequences were categorized in the following five groups: the BBS family, the MGM family, the C-rich family (apparently being indirectly selected by the G-rich MGM), short random regions (possibly resulting from deletion during repeated amplification or cloning), and sequences not belonging to the above families. The ratio of BBS to MGM is dramatically increased in both pools compared to the untreated G9 pool, as indicated in FIGS. 3 and 4. None of the surviving MGM isolates contained any consecutive sequence segment that would be perfectly matched by any marking oligonucleotide used, indicating an effective elimination of the marked species. The relative proportions of the four non-MGM groups are nearly identical in both treated pools. However, there are more MGM in the E. coli RNaseH treated pool than in the one treated with the Hybridase, indicating that treatment with longer marking oligonucleotides at higher temperature by the Hybridase is preferable. Moreover, a new representative consensus can be extracted from the surviving species, in which two adjacent G-triplets are separated by three A or T positions. A new marking oligonucleotide, NCW13 (SEQ ID No: 15), was designed and used in the treatment of another pool selected by a different target, and this improved the efficiency of MGM ablation (see Example 3 infra).

Example 2

Restriction of MGM, BBS, or Both, on the B52 selected G9 Pool

As described herein above, in addition to mining less prevalent RNA aptamer families from a selected pool, this population restriction method can be extended to a general approach for generating different ligands to all of the targets in a mixture. To test the efficiency and versatility of this method, both the MGM family and the BBS family were removed, successively or simultaneously, from the B52 selected G9 pool and its derivatives. The relationship among the pools derived from B52 G9 is shown in FIG. 2. In contrast to the MGM family, the BBS family has a highly homologous, long consensus, and can be marked by two 17-mer sequences with only three positions different between them. The reaction was carried on at a higher temperature, 55° C., when only BBSs were to be eliminated, further increasing the specificity. Depletion of either or both families was confirmed by Southern dot blot analyses with the marking oligonucleotides as probes, as shown in FIG. 3.

Example 3

MGM Restriction on the HSF Selected G9 Pools and Subsequent Selection of an HSF Aptamer To confirm the efficiency of the method developed in previous examples, and to provide a more general case of exhaustive selection and matrix-binding reduction, two other selections were performed against the *Drosophila* heat shock factor (HSF) (Wu, "Heat Shock Transcription Factors: Structure and Regulation", *Ann. Rev. Cell Dev. Biol.* 11:441-469 (1995), which is hereby incorporated by reference in its entirety), which regulates the activation of heat shock gene transcription by binding to specific promoter elements.

The first stage of the selection used as the starting material the same initial unselected RNA pool as that used in the B52 selection, The target HSF was expressed and purified as a GST fusion protein in E. coli. The selection scheme and conditions were almost identical to that used for B52 except the following minor modifications. In one selection (designated L), a negative selection against nitrocellulose filter following the recovery of bound RNA was performed in Cycle 8. In the other selection (designated H), a higher concentration (50 mM) of magnesium ion was used in the binding buffer. Based on the experience with the B52 selection, this stage of selection was expected to yield pools dominated by MGMs. Indeed, when the pools from the seventh and the ninth generations of Selection L were cloned and sequenced, all but one sequence were MGM's. A Southern (dot) blot analysis on the genealogical archives (saved fractions of pools from each cycle of selection) of both experiments with a representative MGM probe showed an effective enrichment of the MGM family over the generations (see Example 4 infra). The contours of the evolutionary trajectories are almost identical with that in the B52 selection, but apparently the MGM family was enriched even more efficiently in Selection L.

Three consecutive RNA restriction treatments were performed on the two G9 pools to eliminate the MGM. The first two treatments were done with the same protocol and reagents that produced B52 G9-M/M, namely, with the "dodecamarker set" (SEQ ID Nos: 10-14) and the Hybridase at 45° C. After examining the sequences of the two B52 G9-M/M pools, a group of surviving MGM was identified and a new marking oligo, NCW13 (SEQ ID No: 15), was designed. The NCW13 was used together with the dodecamarkers in the third treatment of the HSF G9 pool to yield the two G9-M/M/M pools that were cloned. The relationship between pools derived from the two HSF G9 pools is depicted in FIG. 2. Twenty-two individuals from the G9/L-M/M/M pool and twenty-seven from the G9/H-M/M/M pool were sequenced. Compared to the B52 G9-M/M pools, MGMs have been further decreased due to the use of NCW13. Among the remaining isolates about half are C-rich sequences, as was seen in the B52 G9-M/M pools.

Considering the sequence data of these treated pools, it was speculated that a very small fraction of true HSF aptamers may still exist in the final generation (G9) dominated by MGM family. After the MGM restriction treatment, a second stage of selection was performed using the G9/H-M/M/M pool as starting material (designated Generation 9a in FIG. 5A). During this stage, a His-tagged HSF is used as the target; and the magnesium concentration is kept at 5 mM under the condition otherwise identical to that used previously. Three cycles of selection with filter-binding as partitioning method were performed to yield Generations 10, 11, and 12. A negative selection step against nitrocellulose filter following the recovery of bound RNA was included in these cycles as in Cycle 8 of Selection L. Two more cycles using electrophoretic mobility shift as partitioning method were performed to yield Generations 13 and 14. When G14 was cloned and sequenced, five individuals in a sample of 19 have an identical sequence that was subsequently verified to have contained a high-affinity aptamer of HSF (RA1-HSF).

Example 4

Evolutionary Trajectory of the MGM Family in Three Independent Selections

In the above examples, the population restriction method was used to mine less prevalent RNA aptamer families from a selected pool. However, the method can also be used to control the population of an aptamer family, such as MGM, during the selection and before it dominates the pool. The population dynamics of this family in the selection process in the absence of restriction would reveal a proper time point (or generation) for the intervention to begin in order to prevent MGM domination in the selected pools. To this end, the evolutionary trajectories of the MGM family were mapped in all three selection experiments mentioned above. Representative sequences of the MGM family were used as probes to detect the family members and reveal their relative concentration in the DNA pools in a Southern (dot) blot analysis.

Figure 6:
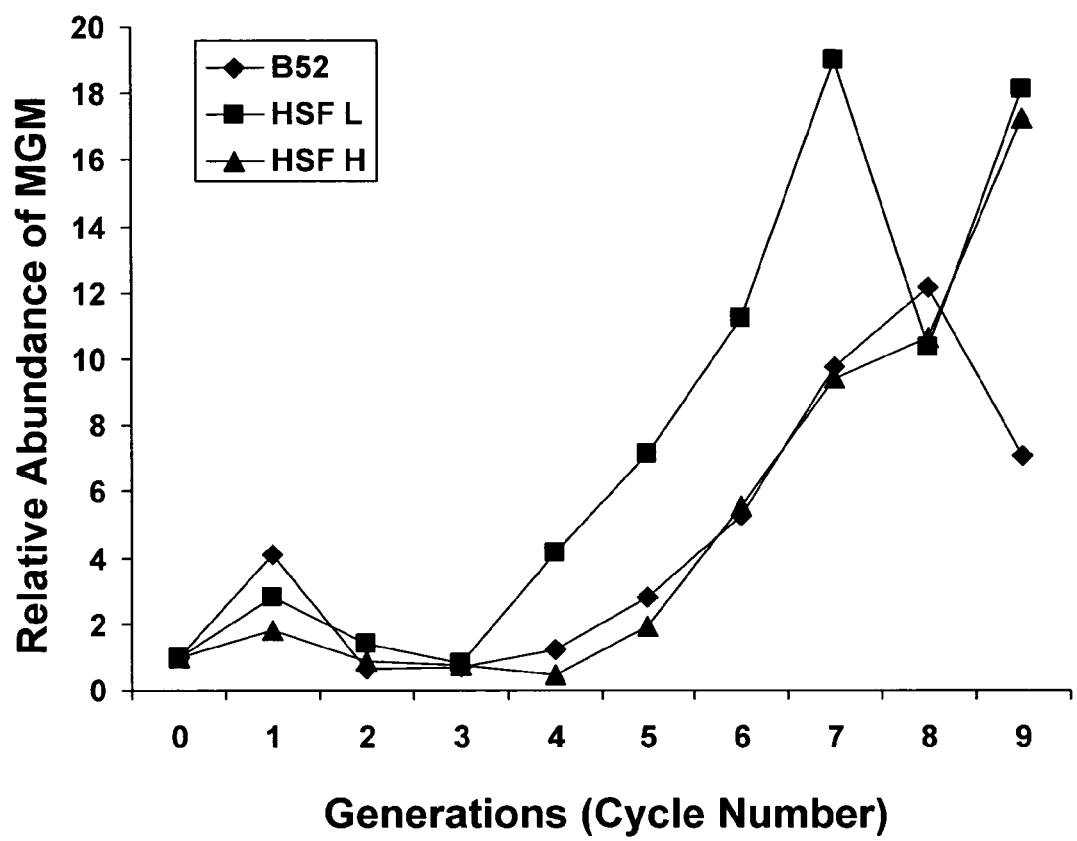
FIG. 6 is a graph that tracks the enrichment of the MGM sequence family in three different selection experiments. The relative abundance of MGM in different generations was measured by Southern dot blot analysis using oligonucleotides representing the MGM consensus sequences as probes. The general shape of the curves was confirmed by examining the filter-binding activity of the RNA pools representing each generation. Arrows indicate negative selection against filter-binding.

Since the spacing between G-triplets varies considerably it is not possible to find a sequence or a small set of sequences long enough to cover all MGM clones. Two short sequences, each containing two G-triplets separated by only one or two nucleotides, were extracted and two more degenerated flanking positions were added to construct the representative probes for the MGM family (SEQ ID Nos: 10 and 11). In all of the blot analyses, the 5' constant region on each sequence was probed (using SEQ ID No: 18) to normalize the signal. As shown in FIG. 6, the time series of relative abundance as probed by these probes revealed a steady enrichment trajectory. They did not become significantly abundant until after Cycle 3. Towards the end, the rate of enrichment slowed down, as there was less selective pressure between the winning clones and the bulk pool. If the RNA restriction method is applied at Cycle 3 and thereafter, the MGM family would not have dominated the final selected pools.

Example 5

Ion Dependence of the MGM Affinity to the Filter

Figure 7:
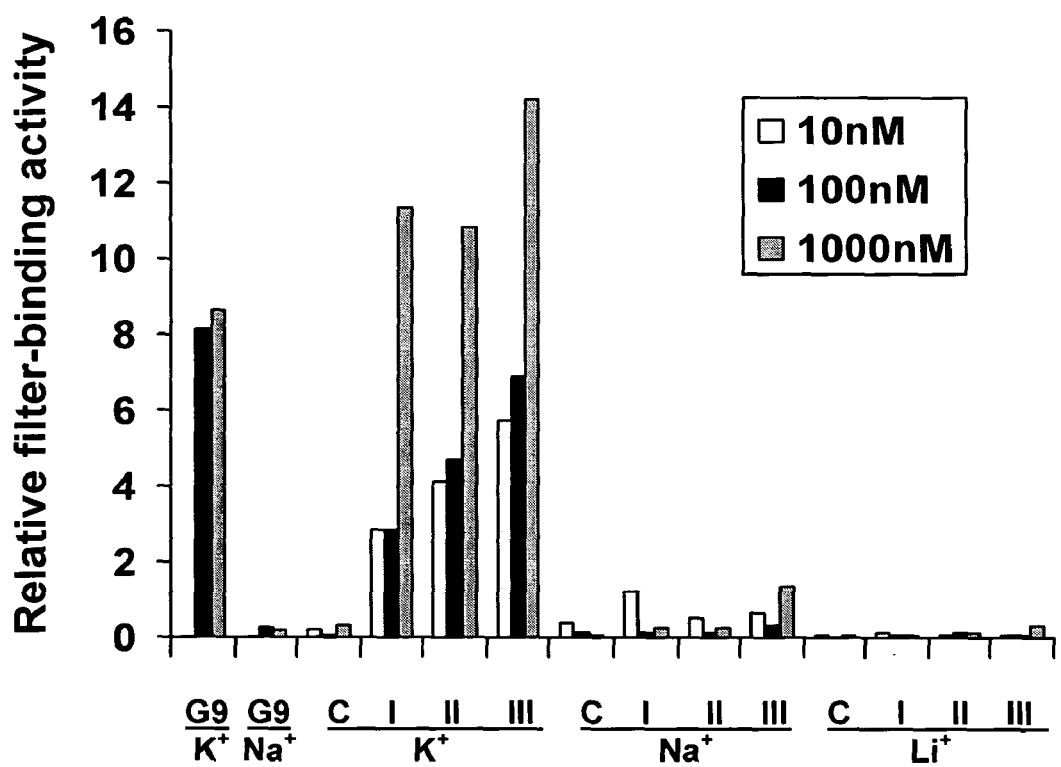
FIG. 7 is a graph that illustrates ion dependency of MGM binding to filters. The binding activity of MGM to the filter was examined in buffers only different in the monovalent ion they contain. Different RNA concentrations were used as indicated. The bulk binding activity of G0 (the un-selected progenitor pool) and G9$^{B52}$ in buffer containing K$^+$ was compared to set the base line activity. The bulk binding activity of G9$^{B52}$ in buffer containing K$^+$ or Na$^+$ was compared to show the sensitivity of the binding activity to Na$^+$. RNAs with three individual MGM sequences and one random sequence were used to further investigate the ion dependency. The sequences of these RNAs (I, II, III, and C in the graph) are as follows.

A possible structure of MGM is suggested by the presence of 4 G-triplets. It has been reported that poly rG can form four-stranded helices (G-quadruplexes) (Zimmerman, et al., "X-ray Fiber Diffraction and Model-building Study of Polyguanylic Acid and Polyinosinic Acid," *J. Mol. Biol.* 92:181-192 (1975), which is hereby incorporated by reference in its entirety). RNAs containing short runs of Gs can also tetramerize (Kim et al., "Tetramerization of an RNA Oligonucleotide Containing a GGGG Sequence," *Nature* 351:33-332 (1991), which is hereby incorporated by reference in its entirety). The quartets of G residues on which such structures depend consist of four guanine bases in a planar array arranged in a cyclic hydrogen-bonding pattern, where each guanine is both the donor and acceptor of two hydrogen bonds between the Hoogsteen and Watson-Crick faces. This arrangement generates a pocket at the center lined by electronegative carbonyl oxygens that is thought to be the site of interaction with a cation. Although such structure is stable in solution, it exhibits a strong dependence of the melting temperature on the monovalent ion present (Williamson, "G-quartet Structures in Telomeric DNA," *Ann. Rev. Biophys. Biomol. Struct.* 23:703-730 (1994), which is hereby incorporated by reference in its entirety). The original binding buffer used in the selection experiment contains 150 mM potassium acetate, which reflects the intracellular concentration of potassium. In a binding reaction, $K^+$ was displaced with identical concentrations of $Na^+$ and $Li^+$. As a result, a dramatic decrease of filter binding activity was observed, almost to the level of the unselected pool (FIG. 7). This result strongly suggests that the MGM sequences form G-quartets or similar structures that are active in binding to the filter, and this feature of MGM can also be explored in the process of selection to decrease the abundance of this family in the pools.

Example 6

Theoretical Foundation for Observed Results

To describe the process of in vitro evolution, the approach of Eigen can be adopted and extended (Eigen, "New Concepts for Dealing with the Evolution of Nucleic Acids," *Cold Spring Harb. Symp. Quant. Biol.* 52:307-320 (1987), which is hereby incorporated by reference in its entirety). Based on the exponential model for single species growth and decay $$\dot{c}_i = k_i c_i(t)$$

where k is growth constant and c is concentration at time t, the clone i (descendants of a single ancestor individual in the original unselected pool) can be followed in terms of relative concentration of its members $$x_i = \frac{c_i}{\sum_l c_l} \quad i = 1, \ldots, n.$$

and its relative growth constant $$k_{i-rel} = k_i - \bar{k}(t)$$

which is its own growth constant ($k_i$) relative in comparison with the average growth constant $$\bar{k}(t) = \Sigma_i k_i x_i(t)$$

The growth constant $k_i$ of a clone i is a function of its member's fitness. The more fit they are to perform the task selected for, the more possible the individuals in the clone will be rewarded to reproduce and, thus, the faster the clone will grow. Because the total number of individuals is limited and fixed in each round of selection to ensure competition, the average growth constant is a function of time and will increase over the cause of the experiment. In each round of selection and amplification, the life cycle of individuals is synchronized; thus, time becomes discrete, analogous to computational updates in parallel processing. For a generic clone in the pool, its growth or decay is described as $$\dot{x}_i = \{k_i - \bar{k}(t)\} x_i(t)$$

$$k_i > \bar{k}(t), \dot{x}_i > 0; \; k_j < \bar{k}(t), \dot{x}_j < 0.$$

Eventually, the average growth constant will aproach the maximal growth constant $k_m$, which is the that of the clone with highest fitness, and this clone (m) will expand to a point where its relative concentration is close to 1. A small sampling at this point will yield multiple isolates of indiviudals belonging to this clone, sometimes along with a few other individuals with growth constant, i.e., fitness, ranking next to it.

If the fitness rank can be altered after the isolation of this first aptamer clone, i.e., if the growth constant of this isolated clone can be decreased to a reduced value $k_{rm}$, so that $$0 \leq k_{rm} < k_m$$

then other aptamer clones with lower previously defined fitness can be identified. In particular, when $k_{rm} < k_{m-1}$, and $x_{m-1} > 0$, the clone m−1 that ranked next to m will be the sure winner of the next stage of selection, if it has not yet been isolated together with m. In general, aptamer clone m−n can be isolated by iteration of this process, until the $(n+1)^{th}$ aptamer shows no specific binding to any known target in the system or its growth rate is indistinguishable from the remaining non-specific binding individuals. Theoretically, this scheme should be exhaustive, as every individual in the original pool with affinity to any target will eventually have a chance to be isolated, one by one, according to their rank of "growth rate."

As the first implementation of this scheme to demonstrate the effect of fitness change in different stages of in vitro evolution, a system with more than one target was sought in which aptamer clones for different targets are expected to "grow" at significantly different rates under well-defined selective conditions. A minimal case should have two targets, either separable or inseparable. (From an operational point of view, separable targets presented in a fixed ratio of concentration are tantamount to a set of inseparable targets.) During the first stage of the selection procedure, selection should yield aptamers for one target; but the isolation of aptamers for the other target in a second stage of the selection procedure would require a fitness change (that reduces the growth constant) for the aptamers previously isolated. The large difference of growth rate in the first stage would contribute to the clarity of the demonstration; and two separable targets would lend analytical ease to this system.

To fulfill these requirements, in Example 3 aptamers for a protein target, the *Drosophila* heat shock factor (HSF), were selected for identification, and aptamers for nitrocellulose filters used in the partitioning step, were selected in different stages of in vitro evolution, all starting from a single ancestral pool of RNA. The heat shock factors regulate the activation of heat shock gene transcription by binding to specific promoter elements. Upon heat treatments, HSF forms homotrimers that bind to specific DNA sequences called heat shock elements (HSEs). Other functions of HSF are not fully understood. *Drosophila* HSF contains at least three domains: a DNA-binding domain, a trimerization domain, and an acidic activation domain. It does not contain any known RNA recognition sequence motifs and is not known to bind to RNA in nature. The filters are chosen as one of the targets, not because of the utility of their aptamers, but because in Example 1 they yielded a fortuitous family of aptamers, named multi-G motifs (MGMs), whose evolutionary trajectories were characterized. Base on these previous results, this aptamer family can be expected to grow at a fast rate under known conditions. The population control procedure was also tested to be effective on this family in Example 2.

The first stage of the selection used as the starting material the same initial unselected RNA pool that previously yielded the MGM family. The target HSF was expressed and purified as a GST fusion protein in *E. coli*. The selection scheme and conditions were almost identical to that described above except that higher magnesium concentration was used to help RNA molecules fold. A Southern dot blot analysis on the genealogical archives (saved fractions of pools from each cycle of selection) with a representative MGM probe showed an effective enrichment of the MGM family through the first to the nine generations (see FIG. 5A), with the contour of its evolutionary trajectory almost identical to that in the selection involving another B52 (see FIG. 6). Sequencing of a single individual isolated from the ninth generation yielded a typical MGM.

Usually a small collection of isolates (10-100 individuals) is sequenced at the end of an experiment to identify selected aptamers. Starting from a pool of $10^{13}$ candidates, this would require a more than $10^{11}$ fold enrichment to see multiple isolates of a clone. And Clone m-1 should have a growth rate close to that of Clone m to be isolated in this sampling. If a lot more individuals in the MGM-dominated G9 were sequenced, then it might have been possible to see aptamers for HSF. But for the purpose of the current study, a second stage of evolution was performed to allow HSF aptamers to dominate the selected pools in an environment where the growth rate of MGMs is reduced asymptotically to zero. This stage can use as starting material any pool in which the relative concentration of any HSF aptamer does not equal zero. The last generation, G9, was selected because the procedure can appropriately be expected to succeed with any other pools from G0 to G8 if success can be achieved with G9, which is the least complex.

Figure 5B:
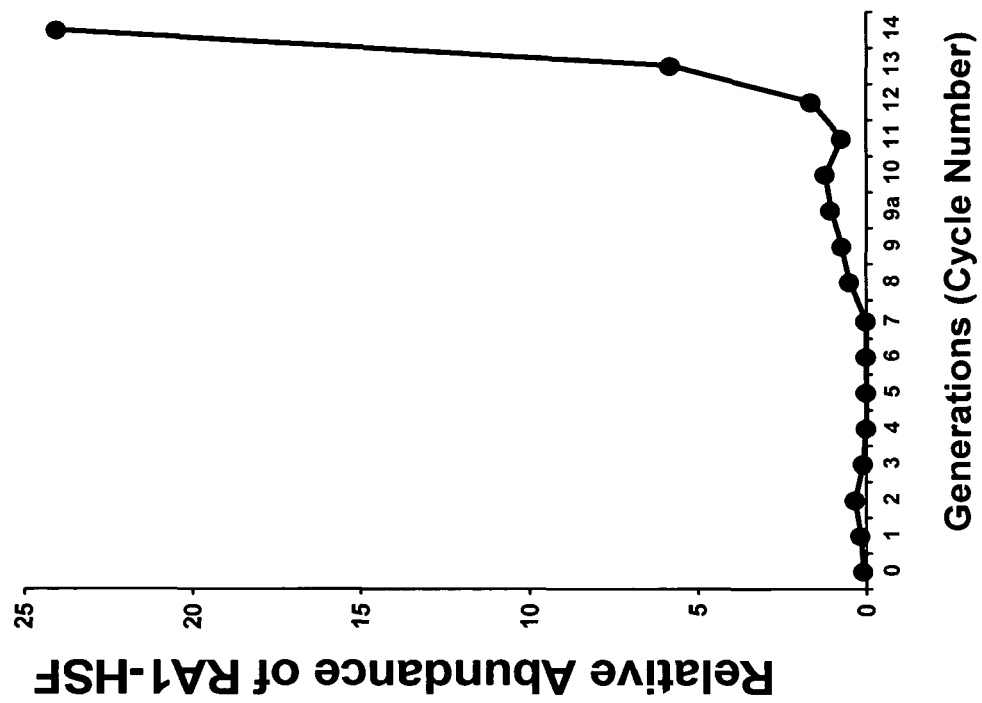
FIGS. 5A-B are graphs that illustrate the change in abundance of the MGM sequence family and the aptamer clone RA1-HSF, respectively, in the two-stage selection leading to the isolation of the HSF aptamer. The relative abundance of MGM in different generations was measured by Southern dot blot analysis using oligonucleotides representing the MGM consensus sequences as probes. The relative abundance of RA1-HSF in different generations was measured by Southern dot blot analysis using sequence of the randomized region of this clone as probe. Abundance is expressed in arbitrary units. Because of sequence variation among the family members and the resulting uneven hybridization efficiency, it is not possible to quantify precisely the abundance of a family, or of one family relative to the other, in one generation. However, the relative abundance detected by the same probe in different generations in the same experiment clearly showed the trends and patterns of enrichment. The affinity of RA1-HSF to HSF has been confirmed by electrophoretic mobility shift assay with different HSF constructs (see FIG. 9A infra). Generations 1 to 9 are those of Selection H. Generation 9a is G9/H-M/M/M.
Figure 5A:
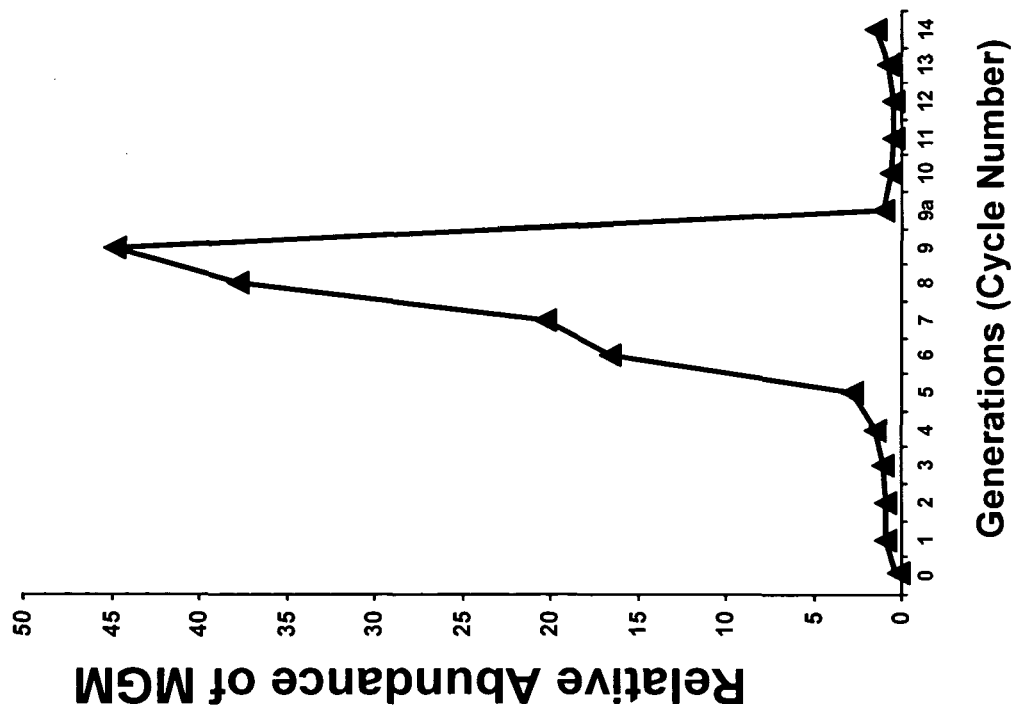

Three consecutive RNA restriction treatments were performed on the G9 pools to eliminate the MGM and generate the pool designated G9a (see FIGS. 5A-5B). The first two treatments were done with the "dodecamarker" set and the last included an additional marking oligo, NCW13. This treatment can also be used in the subsequent rounds of selection to reduce the growth rate of MGM. However, a negative selection (collecting candidates not binding to the filter) is more convenient when the targets are separable. Three cycles of selection with filter-binding as partitioning method were performed with a His-tagged HSF construct to yield Generations 10, 11, and 12. Each of these cycles included a negative selection step against nitrocellulose filter following the recovery of bound RNA. Two more cycles using electrophoretic mobility shift as partitioning method with His-HSF were performed to yield Generations 13 and 14. When G14 was cloned and sequenced, two HSF aptamers dominated the pool, one of them (named RA1-HSF) constituted more than 25% of the sample and showed high affinity to HSF. No MGM showed up in this sample.

The process of this two-stage evolution experiment can be characterized by following the enrichment of MGMs and RA1-HSF through the generations using a Southern (dot) blot analysis on the genealogical archives. The distinct profiles of these two classes of aptamers are shown in FIGS. 5A-5B. To verify these profiles, the G5 and the G9a pools were also cloned and sequenced, in addition to G9 and G14, and present a summary of the sequencing results in Table 1 below.

TABLE 1

Summary of Sequencing Aptamers from
G5, G9, G9a, and G14 Generations

|  | G5 | G9 | G9a | G14 |
|---|---|---|---|---|
| MGMs | 10 | 1 | 1 | 0 |
| C-rich sequences | 7 | 0 | 12 | 3 |
| HSF aptamers | 0 | 0 | 3 | 8 |
| orphan sequences | 13 | 0 | 10 | 9 |
| Total | 30 | 1 | 26 | 20 |
| Multiple isolates | 2x MGM#3 | 0 | 3x #9a-1 | 6x RA1-HSF 2x #14-2 |

According to the model, clones with $k_i$ greater than the average growth constant of the initial pool but lower than $k_m$ would grow (be enriched) during the course of the experiment to a point where $k_i$ is equal to the average growth constant. Then they will decay and eventually become extinct. Sequencing of earlier pools allowed capture of sequences for clones becoming extinct later and tracing of their abundance over generations. The dot blot analysis was used to detect a range of relative concentration $x_i$ of a sequence from 1 to $10^{-3}$, thus even a ten-billion-fold enrichment from $10^{-13}$ to $10^{-3}$ will not be revealed. Nevertheless, a collection of representative clones was obtained and their growth and decay was followed during the second stage of the experiment to provide a well-rounded survey of the process. The sequences of the entire randomized sequence, oligonucleotides 40 bases in length in most cases, were used as probes. These may not be clone-specific, and could pick up signals from a family with a common consensus fragment shorter than the randomized region. In general, members of such a sequence family have similar functional traits.

RA1-HSF is the most abundant clone (6 individuals out of 20 isolates) in the pool G14 (compare graphs of FIG. 8A). It showed the highest affinity among isolated clones in an electrophoretic mobility shift (EMS) assay to HSF. It was not present in the sample from the other three pools. Its enrichment profile showed dramatic growth toward the end of the second stage without sign of slowing rate (FIG. 8A). Clone 14-2 was isolated twice in the G14 sample, and showed a weaker affinity to HSF in an EMS assay (FIG. 8A). It showed a moderate enrichment during the early cycles of the second stage, then decayed towards the end. A similar profile was observed for another clone with weak affinity to HSF, Clone 9a-1 (FIG. 8A). This clone was isolated 3 times in a sample of 26 individuals from G9a, but not present in the sample from G14. One other clone was randomly picked from each of G5 (clone 5-23), G9a (clone 9a-21), and G14 (14-13). Each of them isolated only once. None of them showed detectable affinity to HSF. Their signal in the dot blot analysis cannot be distinguished from the background (FIG. 8B). As shown in FIGS. 8A-B, these results demonstrate a correlation between the aptamers' affinity to HSF and their growth rate during the second stage, providing experimental support to the connection between fitness and growth during in vitro evolution.

As shown in FIG. 9A, the affinity of RA1-HSF to HSF was tested with several different HSF preparations, including GST-HSF, a His-HSF, a MBP-HSF, all purified from bacteria, and baculovirus expressed untagged HSF in crude extract of Sf-9 cells. RA1-HSF can also bind to truncated HSF constructs without the activation domain, suggesting that it probably binds to the DNA binding domain. Estimated from the EMS data, it has a Kd of 20 nM. In contrast, monomeric HSF has very weak affinity to DNA with Kd in the range of μM.

The RA1-HSF clone was further characterized by deletion analysis to define the true aptamer moiety (FIG. 9B). Deleting the 3' constant region and 5 nucleotides next to it did not compromise the affinity of the remaining sequence. However, deletion of the 5' constant region abolished binding capability, indicating that both 5' constant region and the randomized region are parts of the true aptamer.

Without changing the topography of fitness landscape, the conventional in vitro selection and amplification methodology constitutes a single act. From the conventional perspective, the first stage in the above examples is a successful experiment for the isolation of filter-binding aptamers but a failed one with regard to HSF, and second stage was a success for HSF but a failure for the filter-binding aptamers. However, in an experiment with complex targets, the aim is to isolate aptamers for all targets. In the two-target case presented in the above examples, this goal was fulfilled by setting different fitness landscapes for different stages. Throughout the first stage and most of the second stage, the two targets were present in a fixed ratio as if they were inseparable from each other. If they were indeed inseparable, it would not be realistic in the second stage to use positive/negative toggle selection and EMS as a partitioning device. But negative selection against the genotype (sequence) of MGMs tested previously can instead be used. The efficiency of this method is demonstrated here again by the difference in composition between pools G9 and G9a (see FIGS. 5A-5B). Therefore, the procedure presented here can be adopted for experiments with complex inseparable targets with little modification.

In a multi-stage selection scheme, the most fit aptamer clone or clones in one stage are converted to the least fit one(s) in the next stage, thus allowing clones dominate the selected pools in successive stages in an order according to their original rank of fitness in first stage. While the "two-stages-for-two-targets" experiment presented in the above examples is a minimal case, a corresponding number of selection stages for additional targets can be implemented easily according to this same model. Experimentally, negative selection according to genotypes of candidate clones can be executed in an effectively parallel manner. In the above examples, the second stage was started with a pool of low complexity, taking considerable risk of drift caused by both random processes and the MGM restriction treatment. In later stages, though, it would be safer to start with a more complex pool, even the original unselected pool.

RNA aptamers isolated from randomized sequence pools are often embedded in different sequence contexts and possess some variations, constituting an artificial phylogeny. While some "point mutations" were found in different individuals of the RA1-HSF clone, no clones sharing a consensus sequence with it in the randomized region were isolated. The low complexity of the starting pool of the second stage may be a factor contributing to this result. The deletion analysis (FIG. 9B) also suggests that the RA1-HSF aptamer is complex with high information content, and therefore occurs rarely in the unselected pools. With more information about the aptamer, it is possible to address this issue by a positive selection according to genotype. The sequence in the randomized region required for binding to HSF can be used as a probe to isolate containing this segment but different from RA1-HSF.

The HSF plays a central role in cellular stress response. It senses and integrates signals from extracellular and intracellular environments and regulates the expression of heat shock genes whose products are chaperones that help proteins maintain stable folded conformations. Aptamers for HSF can be used as effective molecular probes to study and control this important and complex process.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of identifying RNA ligands which bind to a target molecule, said method comprising:

preparing, through one or more rounds of amplification and selection, a first pool of RNA ligands that collectively bind more than one target, wherein the first pool of RNA ligands comprises one or more predominate target-binding RNA ligands and one or more non-predominate target-binding RNA ligands;

treating the first pool of RNA ligands under conditions effective to reduce the concentration or eliminate the presence of the one or more predominate target-binding RNA ligands from the first pool of RNA ligands;

amplifying the RNA ligands in the treated first pool, thereby forming a second pool of RNA ligands that is enriched in one or more non-predominate target-binding RNA ligands of the first pool but not the one or more predominate target-binding RNA ligands thereof; and identifying from the second pool one or more predominate target-binding RNA ligands that are present in the second pool at a higher concentration than other target-binding RNA ligands.

2. The method according to claim 1 further comprising:

treating the second pool under conditions effective to reduce the concentration or eliminate the presence of one or more predominate target-binding RNA ligands;

amplifying the RNA ligands in the treated second pool, thereby forming a third pool of RNA ligands that is enriched in one or more non-predominate target-binding RNA ligands of the second pool but not the one or more predominate target-binding RNA ligands thereof; and identifying from the third pool one or more predominate target-binding RNA ligands that are present in the third pool at a higher concentration than other target-binding RNA ligands.

3. The method according to claim 2 wherein each said treating comprises:

introducing into the pool to be treated one or more nucleic acid molecules that hybridize to the one or more predominate target-binding RNA ligands to form hybrid complexes and introducing into the pool to be treated an enzyme which cleaves at least the RNA ligand of the hybrid complexes, thereby destroying the one or more predominate target-binding RNA ligands.

4. The method according to claim 1 further comprising repeating said treating, amplifying, and identifying for each subsequent pool until substantially all of the non-predominate target-binding RNA ligands in the first pool have been identified.

5. The method according to claim 4 wherein each said treating comprises:

introducing into the pool to be treated one or more nucleic acid molecules that hybridize to the one or more predominate target-binding RNA ligands to form hybrid complexes and introducing into the pool to be treated an enzyme which cleaves at least the RNA ligand of the hybrid complexes, thereby destroying the one or more predominate target-binding RNA ligands.

6. The method according to claim 5 wherein the one or more nucleic acid molecules are DNA and the enzyme is an RNaseH enzyme.

7. The method according to claim 4 wherein each said identifying comprises:

isolating the one or more predominate target-binding RNA ligands and sequencing the one or more predominate target-binding RNA ligands.

8. The method according to claim 1 wherein said identifying comprises:

isolating the one or more predominate target-binding RNA ligands and sequencing the one or more predominate target-binding RNA ligands.

9. The method according to claim 1 further comprising:

preparing the pool of RNA ligands that collectively bind to more than one target and identifying one or more predominate target-binding RNA ligands.

10. The method according to claim 9 wherein said preparing comprises:

expressing a library of RNA molecules that includes both RNA ligands that bind to at least one of one or more targets and RNA molecules that do not bind any of the one or more targets; and partitioning the library of RNA molecules to form the first pool of RNA ligands.

11. The method according to claim 10 wherein said expressing the library of RNA molecules comprises:
   expressing a library of DNA molecules that includes both DNA ligands that bind to at least one of one or more targets and DNA molecules that do not bind any of the one or more targets; and
   transcribing the library of RNA molecules from the library of DNA molecules.

12. The method according to claim 1 wherein said treating comprises:
   introducing into the first pool one or more nucleic acid molecules that hybridize to the one or more predominate target-binding RNA ligands to form hybrid complexes and
   introducing into the first pool an enzyme which cleaves at least the RNA ligand of the hybrid complexes, thereby destroying the one or more predominate target-binding RNA ligands.

13. The method according to claim 12 wherein the one or more nucleic acid molecules are DNA and the enzyme is an RNaseH enzyme.

14. The method according to claim 1 wherein the targets comprise natural or synthetic small molecules, macromolecules, supramolecular assemblies, and combinations thereof.

15. A method of reducing the concentration or eliminating the presence of unwanted target-binding species from a pool of RNA ligands, said method comprising:
   providing a pool of RNA ligands which includes both wanted and unwanted target-binding RNA ligands;
   isolating one or more unwanted target-binding RNA ligands;
   sequencing the one or more unwanted target-binding RNA ligands;
   introducing into the pool one or more nucleic acid molecules that hybridize to the one or more unwanted target-binding RNA ligands to form hybrid complexes; and
   introducing into the pool an enzyme which cleaves at least the RNA ligands of the hybrid complexes, thereby destroying the one or more unwanted target-binding RNA ligands.

16. The method according to claim 15 wherein the one or more nucleic acid molecules are DNA and the enzyme is an RNaseH enzyme.

17. The method according to claim 15 wherein the one or more unwanted target-binding RNA ligands comprise one or more RNA ligands that bind to a matrix used to partition the pool of RNA ligands from a library of RNA molecules.

18. The method according to claim 15 wherein the unwanted target-binding RNA ligands are RNA ligands that bind to a matrix, and wherein said treating comprises:
   introducing into the pool one or more nucleic acid molecules that hybridize to the RNA ligands that bind to a matrix, thereby forming hybrid complexes and
   introducing into the pool an enzyme which cleaves at least the RNA ligands of the hybrid complexes, thereby destroying the RNA ligands that bind to a matrix.

19. The method according to claim 18 wherein the one or more nucleic acid molecules are DNA and the enzyme is an RNaseH enzyme.

20. The method according to claim 18 wherein the matrix is a nitrocellulose matrix.

21. A method of identifying RNA ligands which bind to a target molecule, said method comprising:
   preparing, through one or more rounds of amplification and selection, a first pool of RNA ligands that collectively bind more than one target, wherein the first pool of RNA ligands comprises one or more predominate target-binding RNA ligands and one or more non-predominate target-binding RNA ligands;
   treating the first pool of RNA ligands under conditions effective to reduce the concentration or eliminate the presence of the one or more predominate target-binding RNA ligands, but not the one or more non-predominate target-binding ligands, from the first pool of RNA ligands;
   amplifying the RNA ligands in the treated first pool, thereby forming a second pool of RNA ligands that is enriched in one or more non-predominate target-binding RNA ligands of the first pool but not the one or more predominate target-binding RNA ligands thereof; and
   identifying from the second pool one or more predominate target-binding RNA ligands that are present in the second pool at a higher concentration than other target-binding RNA ligands.

* * * * *

SEQUENCE LISTING

```
<160> NUMBER OF SEQ ID NOS: 36

<210> SEQ ID NO 1
<211> LENGTH: 39
<212> TYPE: RNA
<213> ORGANISM: Artificial Sequence
<220> FEATURE:
<223> OTHER INFORMATION: Description of Artificial Sequence:
      Nitrocellulose binding sequence

<400> SEQUENCE: 1
aacguagaac caauaagggu augggaaggg uaaaaggga                          39
```

```
<210> SEQ ID NO 2
<211> LENGTH: 50
<212> TYPE: RNA
<213> ORGANISM: Artificial Sequence
<220> FEATURE:
<223> OTHER INFORMATION: Description of Artificial Sequence:
      Nitrocellulose binding sequence

<400> SEQUENCE: 2
cacaacgauc aaaagaaaag ggagggccgg ggaaggguug gacaaacagg              50

<210> SEQ ID NO 3
<211> LENGTH: 50
<212> TYPE: RNA
<213> ORGANISM: Artificial Sequence
<220> FEATURE:
<223> OTHER INFORMATION: Description of Artificial Sequence:
      Nitrocellulose binding sequence

<400> SEQUENCE: 3
gcccacgacc aaaacaaagg gaaggaggga gggugcagac gaaagccagg              50

<210> SEQ ID NO 4
<211> LENGTH: 45
<212> TYPE: RNA
<213> ORGANISM: Artificial Sequence
<220> FEATURE:
<223> OTHER INFORMATION: Description of Artificial Sequence:
      Nitrocellulose binding sequence

<400> SEQUENCE: 4
uacaacaucg uagcguggca acugauggcu uugccgaacu cugaa                   45

<210> SEQ ID NO 5
<211> LENGTH: 8
<212> TYPE: DNA
<213> ORGANISM: Artificial Sequence
<220> FEATURE:
<223> OTHER INFORMATION: Description of Artificial Sequence:  Probe

<400> SEQUENCE: 5 cccttccc                                                             8

<210> SEQ ID NO 6
<211> LENGTH: 8
<212> TYPE: DNA
<213> ORGANISM: Artificial Sequence
<220> FEATURE:
<223> OTHER INFORMATION: Description of Artificial Sequence:  Probe

<400> SEQUENCE: 6 ccctccct                                                             8

<210> SEQ ID NO 7
<211> LENGTH: 8
<212> TYPE: DNA
<213> ORGANISM: Artificial Sequence
<220> FEATURE:
<223> OTHER INFORMATION: Description of Artificial Sequence:  Probe

<400> SEQUENCE: 7 ccctcctt                                                             8

<210> SEQ ID NO 8
<211> LENGTH: 8
<212> TYPE: DNA
```

```
<213> ORGANISM: Artificial Sequence
<220> FEATURE:
<223> OTHER INFORMATION: Description of Artificial Sequence: Probe

<400> SEQUENCE: 8 cccctcca                                                                        8

<210> SEQ ID NO 9
<211> LENGTH: 8
<212> TYPE: DNA
<213> ORGANISM: Artificial Sequence
<220> FEATURE:
<223> OTHER INFORMATION: Description of Artificial Sequence: Probe

<400> SEQUENCE: 9 cccacccg                                                                        8

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: unsure
<222> LOCATION: (1)..(2)
<223> OTHER INFORMATION: N at positions 1-2 can be A, T, G, or C
<220> FEATURE:
<221> NAME/KEY: unsure
<222> LOCATION: (11)..(12)
<223> OTHER INFORMATION: N at positions 11-12 can be A, T, G, or C

<400> SEQUENCE: 10 nnccottccc nn                                                                  12

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: unsure
<222> LOCATION: (1)..(2)
<223> OTHER INFORMATION: N at positions 1-2 can be A, T, G, or C
<220> FEATURE:
<221> NAME/KEY: unsure
<222> LOCATION: (11)..(12)
<223> OTHER INFORMATION: N at positions 11-12 can be A, T, G, or C

<400> SEQUENCE: 11
nnccctccct nn                                                                  12

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: unsure
<222> LOCATION: (1)..(2)
<223> OTHER INFORMATION: N at positions 1-2 can be A, T, G, or C
<220> FEATURE:
<221> NAME/KEY: unsure
<222> LOCATION: (11)..(12)
<223> OTHER INFORMATION: N at positions 11-12 can be A, T, G, or C

<400> SEQUENCE: 12
nnccctccTT nn                                                                  12
```

```
<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: unsure
<222> LOCATION: (1)..(2)
<223> OTHER INFORMATION: N at positions 1-2 can be A, T, G, or C
<220> FEATURE:
<221> NAME/KEY: unsure
<222> LOCATION: (11)..(12)
<223> OTHER INFORMATION: N at positions 11-12 can be A, T, G, or C

<400> SEQUENCE: 13
nnccnctcca nn                                                          12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: unsure
<222> LOCATION: (1)..(2)
<223> OTHER INFORMATION: N at positions 1-2 can be A, T, G, or C
<220> FEATURE:
<221> NAME/KEY: unsure
<222> LOCATION: (11)..(12)
<223> OTHER INFORMATION: N at positions 11-12 can be A, T, G, or C

<400> SEQUENCE: 14
nncccacccg nn                                                          12

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: unsure
<222> LOCATION: (1)..(2)
<223> OTHER INFORMATION: N at positions 1-2 can be A, T, G, or C
<220> FEATURE:
<221> NAME/KEY: unsure
<222> LOCATION: (6)..(8)
<223> OTHER INFORMATION: W at positions 6-8 can be A or T
<220> FEATURE:
<221> NAME/KEY: unsure
<222> LOCATION: (12)..(13)
<223> OTHER INFORMATION: N at positions 12-13 can be A, T, G, or C

<400> SEQUENCE: 15
nncccwwwcc cnn                                                         13

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Probe

<400> SEQUENCE: 16
cggtcgcctg gttgacc                                                     17

<210> SEQ ID NO 17
```

-continued

```
<211> LENGTH: 17
<212> TYPE: DNA
<213> ORGANISM: Artificial Sequence
<220> FEATURE:
<223> OTHER INFORMATION: Description of Artificial Sequence:  Probe

<400> SEQUENCE: 17
ctgtcgccag gttgatc                                                    17

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence:  Probe

<400> SEQUENCE: 18
gtaatacgac tcactatagg gagaattcaa ctgccatcta                           40

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence:  Primer

<400> SEQUENCE: 19
gtaatacgac tcactatagg ctacaacatc gtagcgtgg                            39

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence:  Primer

<400> SEQUENCE: 20
ttcagagttc ggcaaagcca tcagttgcca cgctacgatg ttgta                     45

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence:  Primer

<400> SEQUENCE: 21
gtaatacgac tcactatagg caacgtagaa ccaataag                             38

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence:  Primer

<400> SEQUENCE: 22 tccctttttac ccttcccata cccttattgg ttctacgttg                          40

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence:  Primer

<400> SEQUENCE: 23
```
gtaatacgac tcactatagg cacaacgatc aaaagaa                                37

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 24
cctgtttgtc caaccttcc ccggccctcc cttttctttt gatcgttgtg                   50

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 25
gtaatacgac tcactatagg gcccacgacc aaaacaa                                37

<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 26
cctggctttc gtctgcaccc tccctccttc cctttgtttt ggtcgtggg                   49

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 27
atcgcgatac aaaattaagt tgaacgcgag ttctccatct                             40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence:
    DNA encoding randomized region of RNA aptamer 14-1

<400> SEQUENCE: 28
atcgcgatac aaaattaagt tgaacgcgag ttctccatct                             40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence:
    DNA encoding randomized region of RNA aptamer 14-2

<400> SEQUENCE: 29
aagtagctag gagtccttct cccctcaaaa cagaatgggg                             40

<210> SEQ ID NO 30

```
<211> LENGTH: 40
<212> TYPE: DNA
<213> ORGANISM: Artificial Sequence
<220> FEATURE:
<223> OTHER INFORMATION: Description of Artificial Sequence:
      DNA encoding randomized region of RNA aptamer 9a-1

<400> SEQUENCE: 30
ggcaagctac gcgtcaaata gcaagcacac cgaagacaca                              40

<210> SEQ ID NO 31
<211> LENGTH: 90
<212> TYPE: DNA
<213> ORGANISM: Artificial Sequence
<220> FEATURE:
<223> OTHER INFORMATION: Description of Artificial Sequence:
      DNA coding for RA1-HSF (14-1) aptamer

<400> SEQUENCE: 31
gggagaattc aactgccatc taggcatcgc gatacaaaat taagttgaac gcgagttctc        60
catctagtac tacaagcttc tggactcgat                                         90

<210> SEQ ID NO 32
<211> LENGTH: 90
<212> TYPE: DNA
<213> ORGANISM: Artificial Sequence
<220> FEATURE:
<223> OTHER INFORMATION: Description of Artificial Sequence:
      DNA coding for 14-2 aptamer

<400> SEQUENCE: 32
gggagaattc aactgccatc taggcaagta gctaggagtc cttctcccct caaaacagaa        60
tggggagtac tacaagcttc tggactcgat                                         90

<210> SEQ ID NO 33
<211> LENGTH: 90
<212> TYPE: DNA
<213> ORGANISM: Artificial Sequence
<220> FEATURE:
<223> OTHER INFORMATION: Description of Artificial Sequence:
      DNA coding for 9a-1 aptamer

<400> SEQUENCE: 33
gggagaattc aactgccatc taggcggcaa gctacgcgtc aaatagcaag cacaccgaag        60
acacaagtac tacaagcttc tggactcgat                                         90

<210> SEQ ID NO 34
<211> LENGTH: 90
<212> TYPE: RNA
<213> ORGANISM: Artificial Sequence
<220> FEATURE:
<223> OTHER INFORMATION: Description of Artificial Sequence:  RA1-HSF
      (14-1) aptamer

<400> SEQUENCE: 34
gggagaauuc aacugccauc uaggcaucgc gauacaaaau uaaguugaac gcgaguucuc        60
caucuaguac uacaagcuuc uggacucgau                                         90

<210> SEQ ID NO 35
<211> LENGTH: 90
<212> TYPE: RNA
<213> ORGANISM: Artificial Sequence
<220> FEATURE:
<223> OTHER INFORMATION: Description of Artificial Sequence:
      14-2 aptamer
```

-continued

```
<400> SEQUENCE: 35
gggagaauuc aacugccauc uaggcaagua gcuaggaguc cuucuccccu caaaacagaa         60
ugggagguac uacaagcuuc uggacucgau                                         90

<210> SEQ ID NO 36
<211> LENGTH: 90
<212> TYPE: RNA
<213> ORGANISM: Artificial Sequence
<220> FEATURE:
<223> OTHER INFORMATION: Description of Artificial Sequence:  9a-1 aptamer

<400> SEQUENCE: 36
gggagaauuc aacugccauc uaggcggcaa gcuacgcguc aaauagcaag cacaccgaag         60
acacaaguac uacaagcuuc uggacucgau                                         90
```